(12) United States Patent
Shuros et al.

(10) Patent No.: US 10,905,465 B2
(45) Date of Patent: Feb. 2, 2021

(54) DELIVERY DEVICES AND WALL APPOSITION SENSING

(71) Applicant: CARDIAC PACEMAKERS, INC., St. Paul, MN (US)

(72) Inventors: Allan Charles Shuros, St. Paul, MN (US); Brian Soltis, St. Paul, MN (US); Yinghong Yu, Shoreview, MN (US); Arjun D. Sharma, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 308 days.

(21) Appl. No.: 15/816,334

(22) Filed: Nov. 17, 2017

(65) Prior Publication Data

US 2018/0140328 A1 May 24, 2018

Related U.S. Application Data

(60) Provisional application No. 62/424,743, filed on Nov. 21, 2016.

(51) Int. Cl.
*A61B 17/34* (2006.01)
*A61B 90/00* (2016.01)
(Continued)

(52) U.S. Cl.
CPC .......... *A61B 17/3468* (2013.01); *A61B 90/37* (2016.02); *A61M 25/0074* (2013.01); *A61M 25/0082* (2013.01); *A61N 1/025* (2013.01); *A61N 1/3756* (2013.01); *A61N 1/37512* (2017.08); *A61B 2017/00292* (2013.01); *A61M 2025/0002* (2013.01);
(Continued)

(58) Field of Classification Search
CPC .......... A61B 17/3468; A61B 90/37; A61N 1/37512; A61N 1/025; A61N 1/3756; A61M 25/0074; A61M 25/0082; A61M 2025/0002; A61M 2025/3334; A61M 2025/0578; A61M 2025/058
USPC .......................................................... 607/9
See application file for complete search history.

(56) References Cited

U.S. PATENT DOCUMENTS 4,301,815 A 11/1981 Doring
5,807,399 A 9/1998 Laske et al.
(Continued)

FOREIGN PATENT DOCUMENTS

EP 2818201 B1 7/2016
EP 2658599 B1 10/2016
(Continued)

OTHER PUBLICATIONS

International Search Report and Written Opinion dated Jan. 30, 2018 for International Application No. PCT/US2017/062261.

*Primary Examiner* — Mallika D Fairchild
*Assistant Examiner* — Minh Duc G Pham
(74) *Attorney, Agent, or Firm* — Seager, Tufte & Wickhem LLP

(57) ABSTRACT

A delivery device for delivering an implantable leadless pacing device may include a catheter shaft a distal holding section for receiving the implantable leadless pacing device. In some cases, the delivery device may include a flow-sensing device to determine a pressure or flow-rate of a fluid within the distal holding section. Also included may be a handle assembly and a deployment mechanism to deploy the implantable leadless pacing device.

17 Claims, 22 Drawing Sheets

(51) Int. Cl.
*A61N 1/375* (2006.01)
*A61M 25/00* (2006.01)
*A61N 1/02* (2006.01)
*A61N 1/05* (2006.01)
*A61B 17/00* (2006.01)

(52) U.S. Cl.
CPC ............... *A61M 2205/3334* (2013.01); *A61N 2001/058* (2013.01); *A61N 2001/0578* (2013.01)

(56) References Cited

U.S. PATENT DOCUMENTS

| | | |
|---|---|---|
| 5,908,381 A | 6/1999 | Aznoian et al. |
| 6,181,973 B1 | 1/2001 | Ceron et al. |
| 6,395,017 B1 | 5/2002 | Dwyer et al. |
| 6,409,674 B1 | 6/2002 | Brockway et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,799,037 B1 | 9/2010 | He et al. |
| 7,840,281 B2 | 11/2010 | Kveen et al. |
| 7,993,351 B2 | 8/2011 | Worley et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0129750 A1* | 7/2003 | Schwartz ............... A61K 35/28 435/377 |
| 2005/0209653 A1 | 9/2005 | Herbert et al. |
| 2005/0267555 A1 | 12/2005 | Marnfeldt et al. |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2013/0012925 A1 | 1/2013 | Berthiaume et al. |
| 2013/0035636 A1 | 2/2013 | Beasley et al. |
| 2013/0253342 A1* | 9/2013 | Griswold ............... A61N 1/059 600/486 |
| 2013/0253346 A1 | 9/2013 | Griswold et al. |
| 2014/0018818 A1 | 1/2014 | Somogyi et al. |
| 2014/0094771 A1* | 4/2014 | Li ..................... A61M 5/14526 604/506 |
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0094735 A1 | 4/2015 | Ward et al. |
| 2015/0283376 A1 | 10/2015 | Ollivier et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |

(56) References Cited

U.S. PATENT DOCUMENTS

| | | |
|---|---|---|
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Das et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |

\* cited by examiner

DELIVERY DEVICES AND WALL APPOSITION SENSING

CROSS REFERENCE TO RELATED APPLICATIONS

The present application claims the benefit of and priority to U.S. Provisional Patent Application Ser. No. 62/424,743, filed on Nov. 21, 2016, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering an implantable leadless pacing device may comprise a catheter shaft extending from a proximal end to a distal end thereof, the catheter shaft including a distal holding section located at the distal end of the catheter shaft and defining a cavity therein for receiving the implantable leadless pacing device, a flow-sensing device having operational circuitry configured to determine a pressure or a flow-rate of a fluid within the cavity of the distal holding section, a handle assembly including at least a hub portion attached to the proximal end of the catheter shaft, and a deployment mechanism provided with the handle assembly. The deployment mechanism is configured to deploy the implantable leadless pacing device.

Alternatively or additionally to any of the examples above, in another example, the flow-sensing device may be operationally coupled to a user interface having a display and the operational circuitry of the flow-sensing device may be configured to send an indication of the pressure or flow-rate to the display.

Alternatively or additionally to any of the examples above, in another example, the pressure or flow-rate may indicate a degree of wall apposition between a distal end of the distal holding section and a heart chamber wall.

Alternatively or additionally to any of the examples above, in another example, inclusion of the pressure or flow-rate within a range of values may indicate the wall apposition is acceptable and non-inclusion of the pressure or flow-rate in the range of values may indicate the wall apposition is unacceptable.

Alternatively or additionally to any of the examples above, in another example, the acceptable wall apposition may indicate an acceptable deployment position for the implantable leadless pacing device and the unacceptable wall apposition may indicate an unacceptable deployment position for the implantable leadless pacing device.

Alternatively or additionally to any of the examples above, in another example, the delivery device may further comprise a clock device having operational circuitry configured to record a current dispensing time of the fluid into the cavity of the distal holding section.

Alternatively or additionally to any of the examples above, in another example, the clock device may be operationally coupled to the user interface and the operational circuitry of the clock device may be further configured to send an indication of the current dispensing time to the display.

Alternatively or additionally to any of the examples above, in another example, the flow-sensing device may be operationally coupled to the clock device.

Alternatively or additionally to any of the examples above, in another example, the operational circuitry of the flow-sensing device may be further configured to receive the current dispensing time from the clock device.

Alternatively or additionally to any of the examples above, in another example, the operational circuitry of the flow-sensing device may be configured to send a first signal to the display that may indicate an acceptable deployment position and send a second signal to the display that may indicate an unacceptable deployment position.

Alternatively or additionally to any of the examples above, in another example, the first signal may be sent in response to an inclusion of the pressure or flow-rate in a range of values, within the current dispensing time and the second signal may be sent in response to a non-inclusion of the pressure or flow-rate in the range of values, within the current dispensing time.

Alternatively or additionally to any of the examples above, in another example, the operational circuitry of the clock device may be further configured to receive a set of dispensing times, wherein each dispensing time from the set of dispensing times may have a range of acceptable values at which the pressure or flow-rate may be included within to indicate an acceptable degree of wall apposition between a distal end of the distal holding section and a heart chamber wall, compare the current dispensing time to the set of dispensing times, determine if the current dispensing time is equal to a dispensing time from the set of dispensing times and send a read signal to the flow-sensing device in response to the current dispensing time being equal to the dispensing time.

Alternatively or additionally to any of the examples above, in another example, the non-inclusion of the pressure or flow-rate within the range of acceptable values may indicate an unacceptable degree of wall apposition between the distal end of the distal holding section and the heart chamber wall, and the unacceptable degree of wall apposition may indicate an unacceptable deployment position for the implantable leadless pacing device.

Alternatively or additionally to any of the examples above, in another example, the operational circuitry of the flow-sensing device may determine the pressure or flow-rate of the fluid within the cavity of the distal holding section and may send the indication of the pressure or flow-rate to the display in response to receiving the read signal.

Alternatively or additionally to any of the examples above, in another example, the acceptable degree of wall apposition may indicate an acceptable deployment position for the implantable leadless pacing device.

In another example, a delivery device for delivering an implantable leadless pacing device may comprise a catheter shaft may extend from a proximal end to a distal end thereof, the catheter shaft may include a distal holding section defining a cavity therein for receiving the implantable leadless pacing device, a flow-sensing device may have operational circuitry configured to determine a pressure or flow-rate of a fluid within the cavity of the distal holding section, a handle assembly may include at least a hub portion affixed adjacent to the proximal end of the catheter shaft and a deployment mechanism may be disposed within the handle assembly. The deployment mechanism may be configured to deploy the implantable leadless pacing device.

Alternatively or additionally to any of the examples above, in another example, the flow-sensing device may be operationally coupled to a user interface having a display and the operational circuitry of the flow-sensing device may be further configured to send the pressure or flow-rate to the display.

Alternatively or additionally to any of the examples above, in another example, the delivery device may further comprise a clock device having operational circuitry configured to record a dispensing time of the fluid into the cavity of the distal holding section.

Alternatively or additionally to any of the examples above, in another example, the clock device may be operationally coupled to the user interface and the operational circuitry of the clock device may be further configured to send the dispensing time to the display.

Alternatively or additionally to any of the examples above, in another example, the pressure flow-sensing device may be operationally coupled to the clock device.

Alternatively or additionally to any of the examples above, in another example, the operational circuitry of the flow-sensing device may be further configured to receive the dispensing time from the clock device.

Alternatively or additionally to any of the examples above, in another example, the operational circuitry of the flow-sensing device may be further configured to send a first signal to the display that may indicate an acceptable deployment location and send a second signal to the display that may indicate an unacceptable deployment location.

Alternatively or additionally to any of the examples above, in another example, the first signal may be sent in response to an inclusion of the pressure or flow-rate in a range of values, within the dispensing time and the second signal may be sent in response to a non-inclusion of the pressure or flow-rate in the range of values, within the dispensing time.

In another example, a method of delivering an implantable leadless pacing device using a flow-sensing device having operational circuitry may comprise dispensing a fluid into a cavity of a distal holding section of a delivery system, observing the cavity of the distal holding section using the flow-sensing device in response to the dispensing of the fluid, determining a pressure or flow-rate of the fluid within the holding section based on the observation of the cavity; and sending a signal indicative of the pressure or flow-rate to a display of a user interface based on the determination.

Alternatively or additionally to any of the examples above, in another example, the pressure or flow-rate may indicate wall apposition between a distal end of the distal holding section and a heart chamber wall.

Alternatively or additionally to any of the examples above, in another example, the inclusion of the pressure or flow-rate in a range of values may indicate the wall apposition is acceptable and non-inclusion of the pressure or flow-rate in the range of values may indicate the wall apposition is unacceptable.

Alternatively or additionally to any of the examples above, in another example, the acceptable wall apposition may indicate an acceptable deployment location for the implantable leadless pacing device and the unacceptable wall apposition may indicate an unacceptable deployment location for the implantable leadless pacing device.

Alternatively or additionally to any of the examples above, in another example, the method may further comprise recording a dispensing time of the fluid into the cavity of the distal holding section using a clock device.

Alternatively or additionally to any of the examples above, in another example, the clock device may be operationally coupled to the user interface and the method may further comprise sending the dispensing time to the display using the clock device.

Alternatively or additionally to any of the examples above, in another example, the flow-sensing device may be operationally coupled to the clock device and the method may further comprise sending the dispensing time to the flow-sensing device, using the clock device, sending a first signal to the display indicating an acceptable deployment location, using the flow-sensing device, and sending a second signal to the display indicating an unacceptable deployment location, using the flow-sensing device.

Alternatively or additionally to any of the examples above, in another example, the first signal may be sent in response to an inclusion of the pressure or flow-rate in a range of values, within the dispensing time and the second signal may be sent in response to a non-inclusion of the pressure or flow-rate in the range of values, within the dispensing time.

In another example, a delivery device for delivering an implantable leadless pacing device may comprise a catheter shaft extending from a proximal end to a distal end thereof, the catheter shaft may include a distal holding section defining a cavity therein for receiving the implantable leadless pacing device. A clock device having operational circuitry configured to record a dispensing time of a fluid into the cavity of the distal holding section and send the dispensing time to a display on a user interface, a flow-sensing device having operational circuitry that may be configured to determine a pressure or flow-rate of the fluid within the cavity of the distal holding section, send the pressure or flow-rate to the display, and determine a correlation between the pressure or flow-rate and the dispensing time, wherein the correlation may indicate a degree of wall apposition between a distal end of the distal holding section and a heart chamber wall. The delivery device may further include a handle assembly including at least a hub portion affixed adjacent to the proximal end of the catheter shaft and a deployment mechanism disposed within the handle assembly. The deployment mechanism is configured to deploy the implantable leadless pacing device.

Alternatively or additionally to any of the examples above, in another example, an acceptable degree of wall apposition indicates an acceptable deployment location for the implantable leadless pacing device and an unacceptable degree wall apposition indicates an unacceptable deployment location for the implantable leadless pacing device.

Alternatively or additionally to any of the examples above, in another example, the operational circuitry of the flow-sensing device may be further configured to send a first signal to the display indicating the acceptable deployment location and send a second signal to the display indicating the unacceptable deployment location.

Alternatively or additionally to any of the examples above, in another example, the first signal may be sent in response to an inclusion of the pressure or flow-rate in a range of values, within the dispensing time and the second signal may be sent in response to a non-inclusion of the pressure or flow-rate in the range of values, within the dispensing time.

BRIEF DESCRIPTION OF THE DRAWINGS

The disclosure may be more completely understood in consideration of the following detailed description in connection with the accompanying drawings, in which.

Figure 1A:
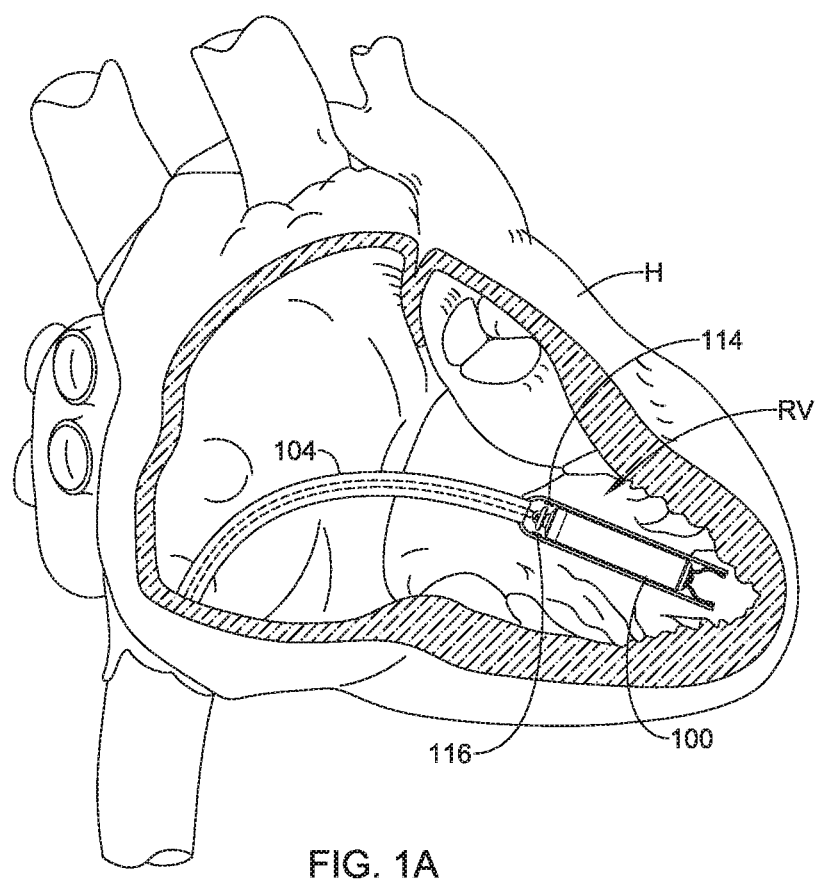
FIGS. 1A-1E are views of an illustrative delivery device that may be used to deliver an implantable leadless cardiac pacing device in a chamber of a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. In other instances, the delivery device may be advanced to the heart via a radial approach or jugular approach, for example. Accordingly, it may be desirable to provide delivery devices which facilitate advancement through the vasculature. Furthermore, the delivery devices can include fluid (e.g., saline) flow-sensing devices that include pressure sensors and/or flow-rate sensors to facilitate acceptable positioning and placement of the capsule in the right ventricle.

Figure 1B:
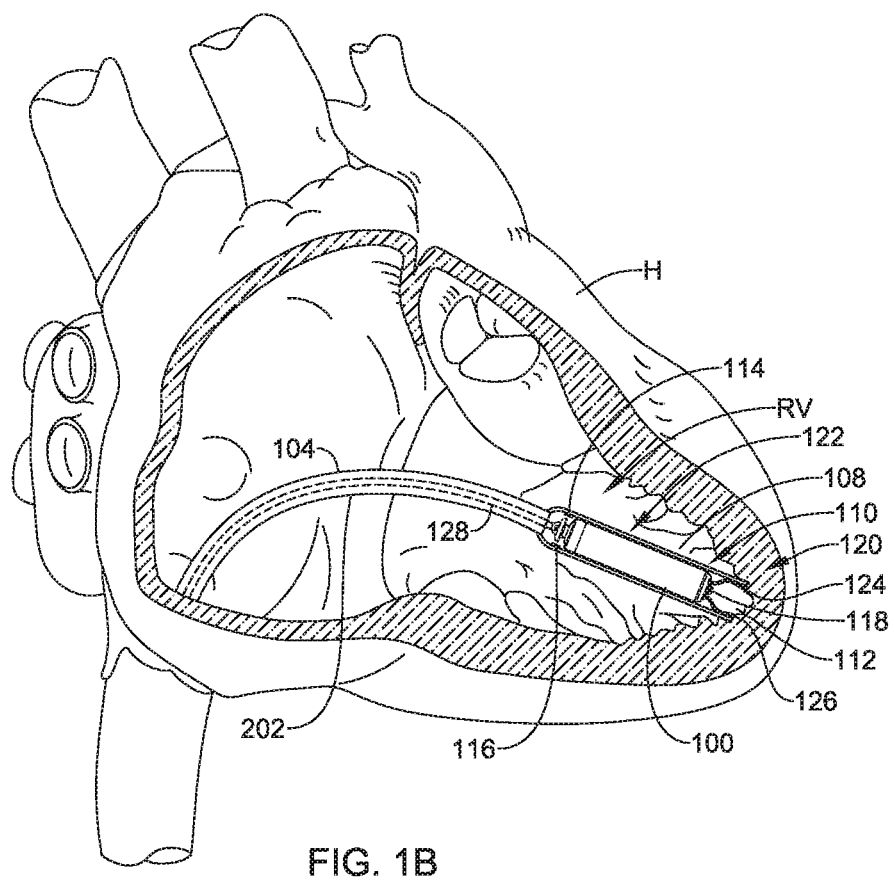

FIG. 1A is a view of an illustrative delivery device 104 (e.g., a catheter) that may be used to deliver an implantable leadless cardiac pacing device 100 (e.g., a leadless pacemaker) in a chamber of a heart H, such as the right ventricle RV. FIG. 1B is a view of an illustrative distal portion 122 of the delivery device 104 that may be used to deliver the implantable device 100. The delivery device 104 may include a distal holding section 108 that may define a cavity 118 for slidably receiving the implantable device 100, and may include a distal opening 112 at a distal end 110 for slidable insertion and/or extraction of the implantable device 100 into and/or out of the cavity 118. Furthermore, the delivery device 104 may include one or more, or a plurality of flow-sensing devices such as sensors 114 and 116, that may sense the pressure of a fluid within the cavity 118 and/or sense the flow-rate of the fluid within the cavity 118 during the delivery process. Also two flow-sensing devices 114 and 116 are discussed herein, it is contemplated that the delivery device 104 may include a single flow-sensing device 114 or 116, or one or more additional flowing-sensing devices in addition to or as an alternative to the flow-sensing devices 114 and/or 116.

During delivery of the implantable device 100 with the delivery device 104, the distal end 110 of the distal holding section 108 may be placed next to and in contact with a wall 120 of the chamber of heart H. The delivery device 104 may then dispense a fluid (e.g., saline) from a port in a handle assembly (e.g., a syringe, a pump coupled to the port, etc.) of the delivery device 104. The fluid may then pass through a lumen 120 of a catheter shaft 202 into the cavity 118 of the distal holding section 108 containing the implantable device 100. As the fluid is dispensed, the flow-sensing devices 114 and 116 may detect the pressure and/or the flow-rate of the fluid within the cavity 118. In various embodiments, the extent and time at which the pressure of the fluid builds inside the cavity 118 and/or the flow-rate of the fluid decreases may depend on the degree of wall apposition between the distal end 110 and the chamber wall 120. In some cases, the degree of wall apposition may be sufficient so that the entire circumference of the distal end 110 of the distal holding section 108 is positioned adjacent to the chamber wall 120, creating a seal between the distal opening 112 and the chamber wall 120. The flow-sensing devices 114 and 116 may then detect that the pressure of the fluid increases inside the cavity 118 to a pressure in an acceptable range in an acceptable amount of time. Alternatively or additionally, flow-sensing devices 114 and 116 may then detect that the flow-rate of the fluid decreases inside the cavity 118 to an acceptable range in an acceptable amount of time. Therefore, the distal holding section 108 may be positioned appropriately to the chamber wall 120 (e.g., with the central longitudinal axis of the implantable device 100 substantially perpendicular to the plane of the tissue in contact with the distal opening 112), thus, increasing the likelihood of acceptable implantation of the implantable device 100. In other cases, the degree of wall apposition may be insufficient and the distal end 110, or at least a portion of the circumference thereof, is not positioned adjacent to the chamber wall, allowing the fluid to leak out of the cavity 118 through the distal opening 112. As a result, the flow-sensing devices 114 and 116 may detect that the pressure of the fluid is not increasing to a pressure in an acceptable range inside the cavity 118 in an acceptable amount of time. Alternatively or additionally, flow-sensing devices 114 and 116 may detect that the flow-rate of the fluid is not decreasing to a flow-rate in an acceptable range inside the cavity 118 in an acceptable amount of time. This may indicate that the distal holding section 108 is not positioned appropriately to the chamber wall and repositioning of the distal holding section 108 may be necessary prior to deployment of the implantable device 100.

Figure 1C:
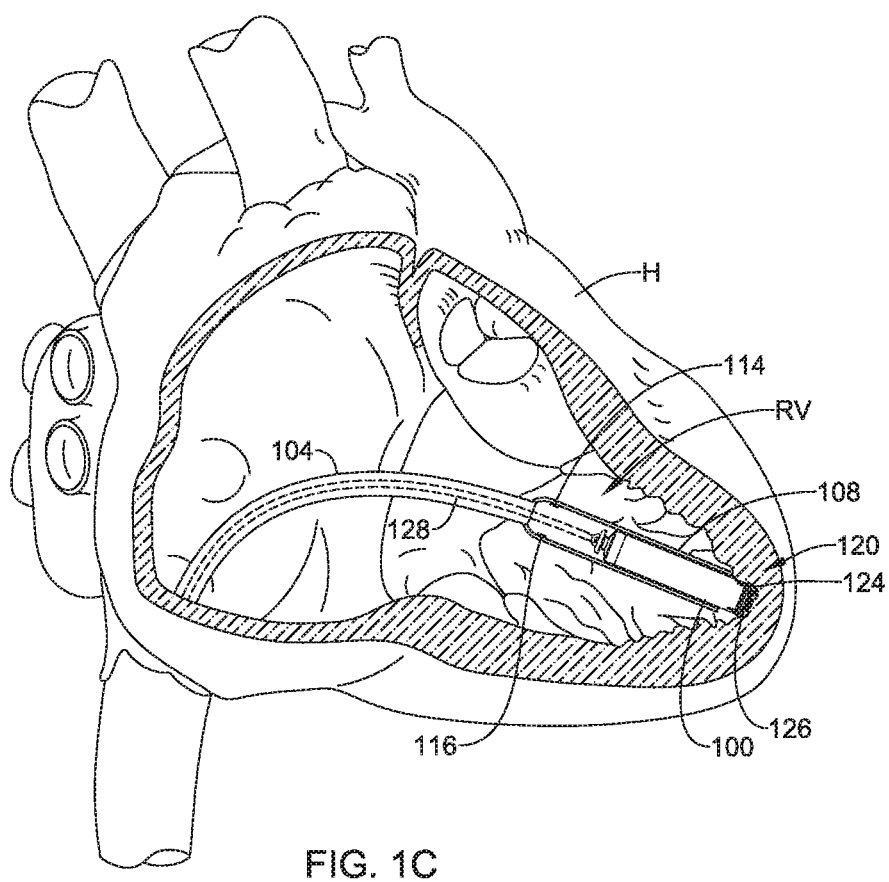
Figure 1D:
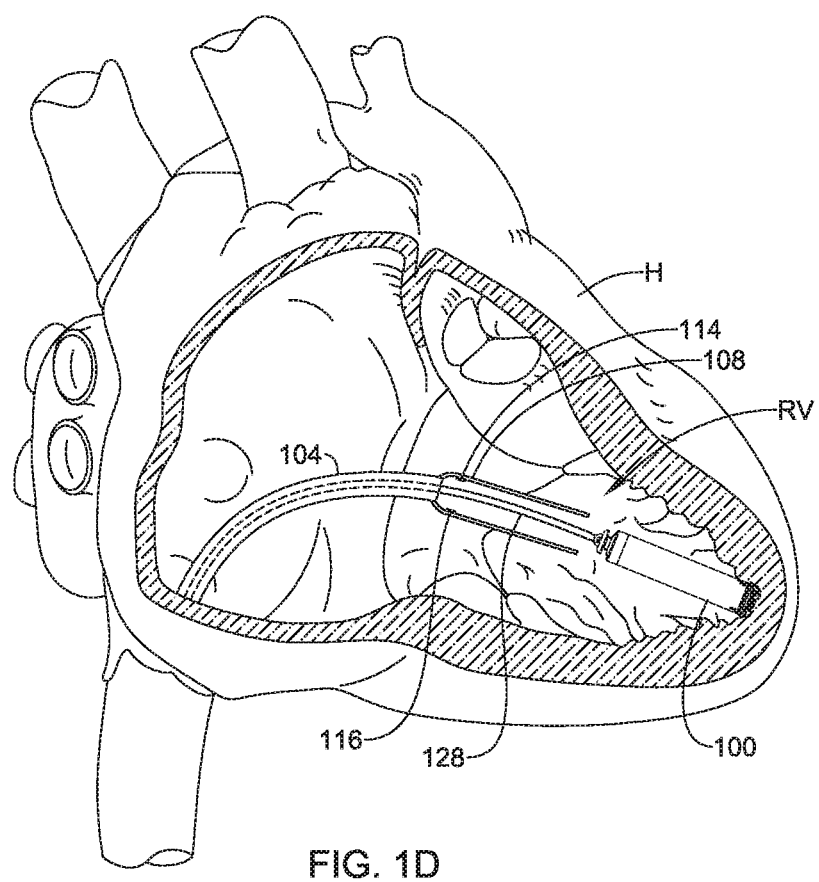
Figure 1E:
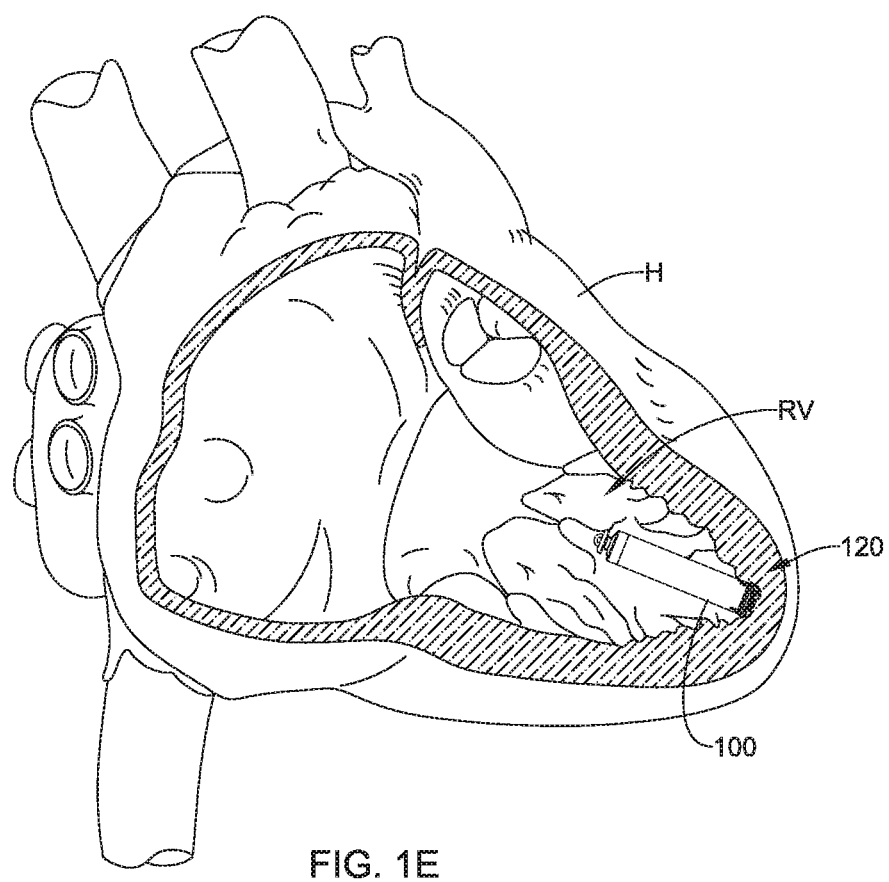

Once an implantation position has been verified by an acceptable pressure and/or flow-rate reading from the flow-sensing devices 114 and 116, deployment of the device 100 can begin. FIG. 1C is a view of an implanted implantable device 100 by the delivery device 104. As the implantable device 100 is pushed distally, a fixation device, hooks or tines 124 and 126 (shown in FIG. 1B), engage the heart tissue of the chamber wall 120. The device 100 may be distally advanced out of the distal holding section 108 to deploy the hooks or tines 124 and 126 from the distal holding section 108 to engage the hooks or tines 124 and 126 in the heart tissue. Once the hooks or tines 124 and 126 have sufficiently engaged the heart wall, as shown in FIG. 1D, the remainder of the implantable device 100 may be expelled from the distal holding section 108 and the delivery device may be retracted. An example of a completed implantation of the implantable device 100 in the chamber of the heart H is shown in FIG. 1E. In other instances, the fixation device may be a helical screw rotationally screwed into the heart tissue of the chamber wall 120 to secure the implantable device 100 to the heart tissue.

Figure 2:
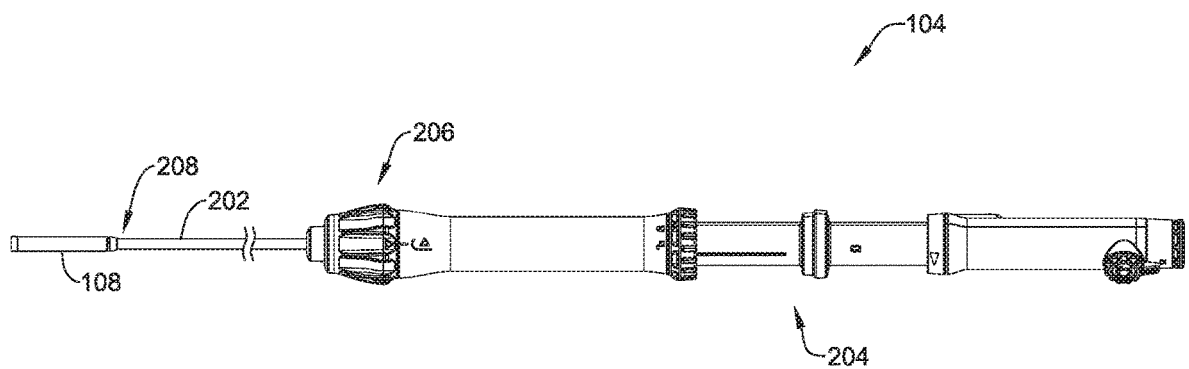
FIG. 2 is a view of an illustrative delivery device.

One aspect of the current disclosure relates to a delivery device and/or system used, for example, to deliver device 100 to a suitable location within the anatomy (e.g., the heart). FIG. 2 is a view of an illustrative delivery device 104, such as a catheter, that may be used to deliver the implantable device 100. The delivery device 104 may include a catheter shaft 202, a handle assembly 204, a deployment mechanism 206, and the distal holding section 108 located at a distal portion 208 of the catheter shaft 202. As may be appreciated, the catheter shaft 202 may need to be navigated, using the handle assembly 204 and the deployment mechanism 206, through relatively tortuous anatomy to deliver the device 100 to a suitable location. For instance, in some embodiments, the catheter shaft 202 may be advanced through the vasculature to a target region. In some example cases the catheter shaft 202 may be advanced through a femoral vein, into the inferior vena cava, into the right atrium, through the tricuspid valve, and into the right ventricle. The target region for the delivery of the device 100 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery device 104 with certain features that may allow for easier or better control for navigation or delivery purposes. When the distal holding section 108 is at a target region and a distal tip portion of the holding section 108 has engaged the heart wall, the deployment positon analysis may begin.

Figure 3:
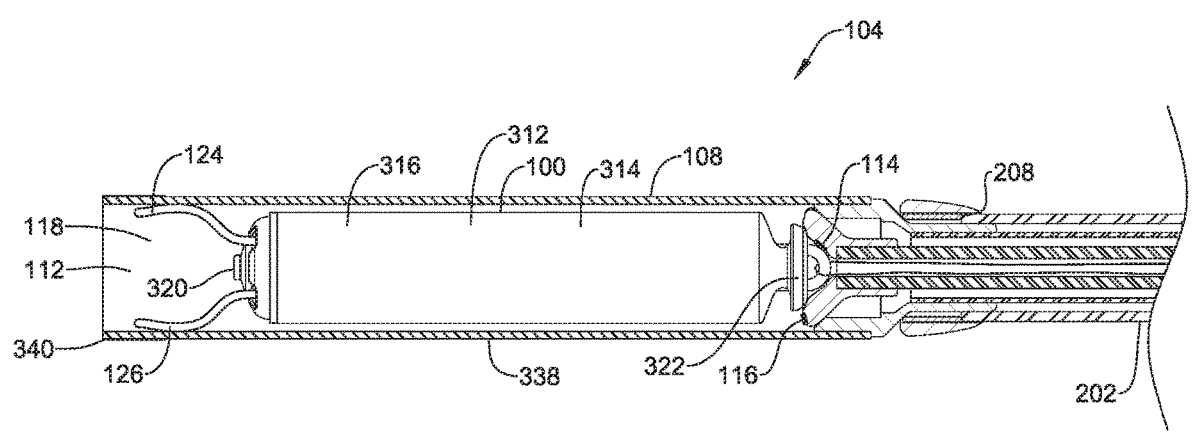
FIG. 3 is a cross-sectional view of the distal portion of a delivery device.

Referring now to FIG. 3, which illustrates a cross-sectional view of the distal portion 208 of delivery device 104, the holding section 108 may define the cavity 118 for slidably receiving the implantable device 100, and may include a distal opening 112 for slidable insertion and/or extraction of the implantable device 100 into and/or out of the cavity 118.

The distal holding section 108 may include a body portion 338 and a distal tip portion 340 that may, for example, be configured to be atraumatic to anatomy, such as a bumper tip. For example, as the catheter shaft 202 is navigated through the anatomy, the distal tip 340 may come into contact with anatomy. Additionally, when the catheter shaft 202 is used to deliver the device 100, the tip 340 of the delivery device 104 will likely come into contact with tissue adjacent the target site (e.g. cardiac tissue of the heart). A hard distal tip formed of the material of the distal portion 208 of the catheter shaft 202 may injure a vessel wall or cardiac tissue. As such, it may be desirable to provide the delivery device 104 with a softer distal tip 340 that can be introduced into the anatomy and come into contact with anatomy adjacent the target cite without causing unnecessary trauma.

For example, the distal tip 340 may be made of a material that is softer than the body portion 338 of the distal holding section 108. In some cases, the distal tip 340 may include a material that has a durometer that is less than the durometer of the material of the body portion 338. In some particular embodiments, the durometer of the material used in the distal tip 340 may be in the range of about 5 D to about 70 D, or for example, in the range of about 25 D to about 65 D. Additionally, the distal tip 340 may include a shape or structure that may make it less traumatic to tissue. For example, the distal tip 340 may have a distal surface, such as a tissue contacting surface, that is rounded or includes a curvature configured to be more atraumatic to tissue.

In some embodiments, all or a portion of the distal holding section 108 may include an inner surface that may be configured to resist getting caught on a fixation mechanism, such as the one or more, or a plurality of hooks or tines 124 and 126 on the device 100. For example, the distal holding section 108 may include an inner layer or coating of harder or more lubricious material that resists force applied by the hooks or tines 124 and 126 onto the inner surface of the distal holding section 108. For example, the distal holding section 108 may include a multi-layered structure, and an inner layer may be made of a material that is harder than an outer layer.

The implantable device 100 may include a shell or housing 312 having a proximal end 314 and a distal end 316. The implantable device 100 may include a first electrode 320 positioned adjacent to the distal end 316 of the housing 312 and a second electrode 322 positioned adjacent to the proximal end 314 of the housing 312. For example, housing 312 may include a conductive material and may be insulated along a portion of its length. A section along the proximal end 314 may be free of insulation so as to define the second electrode 322. The electrodes 320, 322 may be sensing and/or pacing electrodes to provide electro-therapy and/or sensing capabilities. The first electrode 320 may be capable of being positioned against or may otherwise contact the cardiac tissue of the heart H while the second electrode 322 may be spaced away from the first electrode 320, and thus spaced away from the cardiac tissue.

According to various embodiments, the delivery device 104 may also include the flow-sensing devices 114 and 116 that may sense the pressure and/or the flow-rate of the fluid that is dispensed within the cavity 118 of the holding section during the delivery process. The flow sensing devices 114 and 116 used in conjunction with the delivery system (e.g., delivery device 104) may have several different embodiments and configurations. For example, force collector pressure sensors may use a force collector, such as a diaphragm, piston, bourdon tube, or bellows, to measure strain or deflection due to pressure.

In certain embodiments, the delivery device may use piezoresistive strain gauge pressure sensors. A piezoresistive strain gauge pressure sensor may use the piezoresistive effect of bonded or formed strain gauges to detect strain due to applied pressure. Common technology types include silicon (e.g., monocrystalline), polysilicon thin film, bonded metal foil, thick film, and sputtered thin film. In various embodiments, the piezoresistive strain gauge pressure sensors are connected to form a Wheatstone bridge circuit to maximize the output of the sensor and to reduce sensitivity to errors.

In certain embodiments, the delivery device may use capacitive pressure sensors. Capacitive pressure sensors may use a diaphragm and pressure cavity to create a variable capacitor to detect strain due to applied pressure. In various embodiments, the capacitive pressure sensors may use metal, ceramic, or silicon diaphragms.

In certain embodiments, the delivery device may use electromagnetic pressure sensors. Electromagnetic pressure sensors may measure the displacement of a diaphragm by means of inductance, linear variable differential transformation (LVDT), Hall Effect, or by eddy current.

In certain embodiments, the delivery device may use piezoelectric pressure sensors. Piezoelectric pressure sensors may use the piezoelectric effect in certain materials such as quartz to measure the strain upon the sensing mechanism due to pressure. This technology is commonly employed for the measurement of highly dynamic pressures.

In certain embodiments, the delivery device may use optical pressure sensors. Optical pressure sensors may use of the physical change of an optical fiber to detect strain due to applied pressure. A common example of this type utilizes Fiber Bragg Gratings. This technology is employed in applications where the measurement may be highly remote, under high temperature, or may benefit from technologies inherently immune to electromagnetic interference. Another technique utilizes an elastic film constructed in layers that can change reflected wavelengths according to the applied pressure.

In certain embodiments, the delivery device may use potentiometric pressure sensors. Potentiometric pressure sensors may use the motion of a wiper along a resistive mechanism to detect the strain caused by applied pressure.

In certain embodiments, the delivery device may use resonant pressure sensors. Resonant pressure sensors may use changes in resonant frequency to measure stress caused by applied pressure. Resonant pressure sensors may use vibrating wire, vibrating cylinders, quartz, and silicon MEMS.

In certain embodiments, the delivery device 104 may use flow-rate sensing devices that have several different embodiments and configurations. For example, certain methods may rely on forces produced by the fluid as it overcomes a known constriction, to indirectly calculate flow-rate. In some cases, the flow-rate may be measured by measuring the velocity of the fluid over a known area (e.g., at the dispensing location into the cavity 118).

In certain embodiments, the delivery device 104 may use pressure-based flow-rate sensors, such as venture meters, orifice plates, Dall tubes, cone meters, or linear resistance meters. In some cases, the delivery device 104 may use electromagnetic flow-rate sensors, such as magnetic flow meters, non-contact electromagnetic flow meters, ultrasonic flow meters, or Coriolis flow meters. In some instances, the delivery device 104 may use optical flow meters, such as laser-based flow meters or photodetectors. This list is not exhaustive and other flow-rate sensors are contemplated.

According to various embodiments, the pressure of the fluid (e.g., saline) within the distal holding section 108 of the deliver)/device 104 and/or the flow-rate of the fluid within the distal holding section 108 of the delivery device 104, may determine a degree of wall apposition between the distal end 110 of the distal holding section 108 and the heart chamber wall 120. Furthermore, in certain embodiments, the fluid pressure may need to be within a certain range of pressure values and/or the flow-rate may need to be within a certain range of flow-rate values to indicate that the degree of wall apposition is acceptable and the distal holding section 108 is in an acceptable position to deploy the implantable leadless pacing device 100. For example, the pressure value range, ranging from 10 mm Hg to 150 mm Hg, may indicate that the degree of wall apposition, thus, the position of the distal holding section 108 is acceptable. In another example, the range of pressure values may be 60 mm Hg to 120 mm Hg to indicate the position of the distal holding section 108 is acceptable. In another example, the range of pressure values may be 20 mm Hg to 120 mm Hg to indicate the position of the distal holding section 108 is acceptable. In another example, the range of pressure values may be 30 mm Hg to 100 mm Hg to indicate the position of the distal holding section 108 is acceptable. In another example, the range of pressure values may be 80 mm Hg to 110 mm Hg to indicate the position of the distal holding section 108 is acceptable.

In other embodiments, the range of acceptable pressure values may vary with respect to time. For example, fluid may be dispensed from the port in the handle assembly (e.g., a syringe, a pump coupled to the port, etc.) through the lumen 120 of the catheter shaft 202 into the cavity 118 of the distal holding section 108. If the distal end 110 is adjacent to the chamber wall 120, it may be expected that the fluid pressure would increase as time goes by. Therefore, in certain embodiments, after 1 second of fluid delivery, the range of pressure values may be from 10 mm Hg to 50 mm Hg, to indicate the position of the distal holding section 108 is acceptable. After 2 seconds of fluid delivery, the range of pressure values may be from 50 mm Hg to 80 mm Hg, to indicate the position of the distal holding section 108 is acceptable. After 3 seconds of fluid delivery, the range of pressure values may be from 80 mm Hg to 120 mm Hg, to indicate the position of the distal holding section 108 is acceptable. After 4 seconds of fluid delivery, the range of pressure values may be from 120 mm Hg to 150 mm Hg, to indicate the position of the distal holding section 108 is acceptable. Furthermore, if the fluid pressure was to fall outside any of the acceptable ranges of pressure during the fluid dispensing time, an operator can determine that the distal holding section 108 is not positioned correctly and stop the delivery device 104 from dispensing fluid and/or prevent deployment of the implantable device 100.

In further embodiments, the flow-rate value range, ranging from 1.5 mL/s to 4 mL/s, may indicate that the degree of wall apposition, thus, the position of the distal holding section 108 is acceptable. In another example, the range of pressure values may be 2 mL/s to 3.5 mL/s to indicate the position of the distal holding section 108 is acceptable. In another example, the range of pressure values may be 1.5 mL/s to 3.5 mL/s to indicate the position of the distal holding section 108 is acceptable. In another example, the range of pressure values may be 1.75 mL/s to 3.25 mL/s to indicate the position of the distal holding section 108 is acceptable. In another example, the range of pressure values may be 2 mL/s to 3 mL/s to indicate the position of the distal holding section 108 is acceptable.

In other embodiments, the range of acceptable flow-rate values may vary with respect to time. For example, fluid may be dispensed as described above. If the distal end 110 is adjacent to the chamber wall 120, it may be expected that the fluid flow-rate would decrease as time goes by. Therefore, in certain embodiments, after 1 second of fluid delivery, the range of flow-rate values may be from 3.5 mL/s to 4 mL/s, to indicate the position of the distal holding section 108 is acceptable. After 2 seconds of fluid delivery, the range of pressure values may be from 3 mils to 3.5 mL/s, to indicate the position of the distal holding section 108 is acceptable. After 3 seconds of fluid delivery, the range of pressure values may be from 2.5 mils to 2 mL/s, to indicate the position of the distal holding section 108 is acceptable. After 4 seconds of fluid delivery, the range of pressure values may be from 1.5 mils to 2 mils, to indicate the position of the distal holding section 108 is acceptable. Furthermore, if the fluid flow-rate was to fall outside any of the acceptable ranges of flow-rate during the fluid dispensing time, an operator can determine that the distal holding section 108 is not positioned correctly and stop the delivery device 104 from dispensing fluid and/or prevent deployment of the implantable device 100.

Figure 4A:
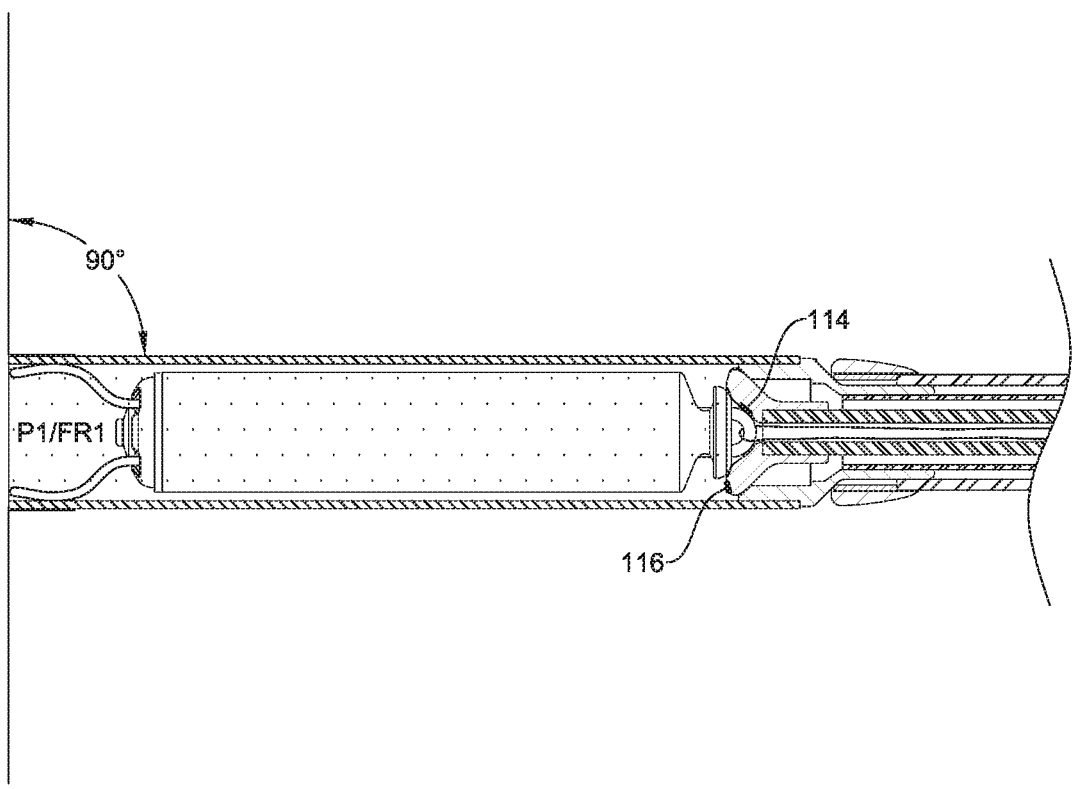
FIGS. 4A-4C illustrate an example of implementation of the pressure sensing device for deploying an implantable leadless cardiac pacing device into a chamber of a heart.
Figure 4B:
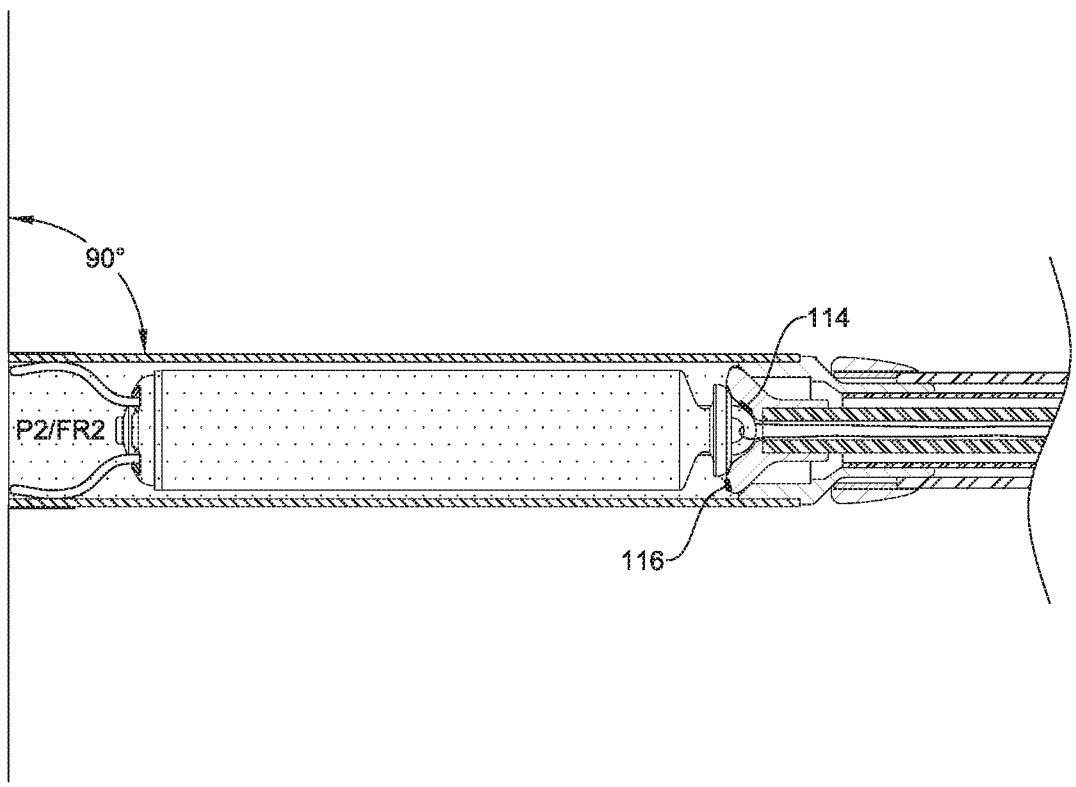
Figure 4C:
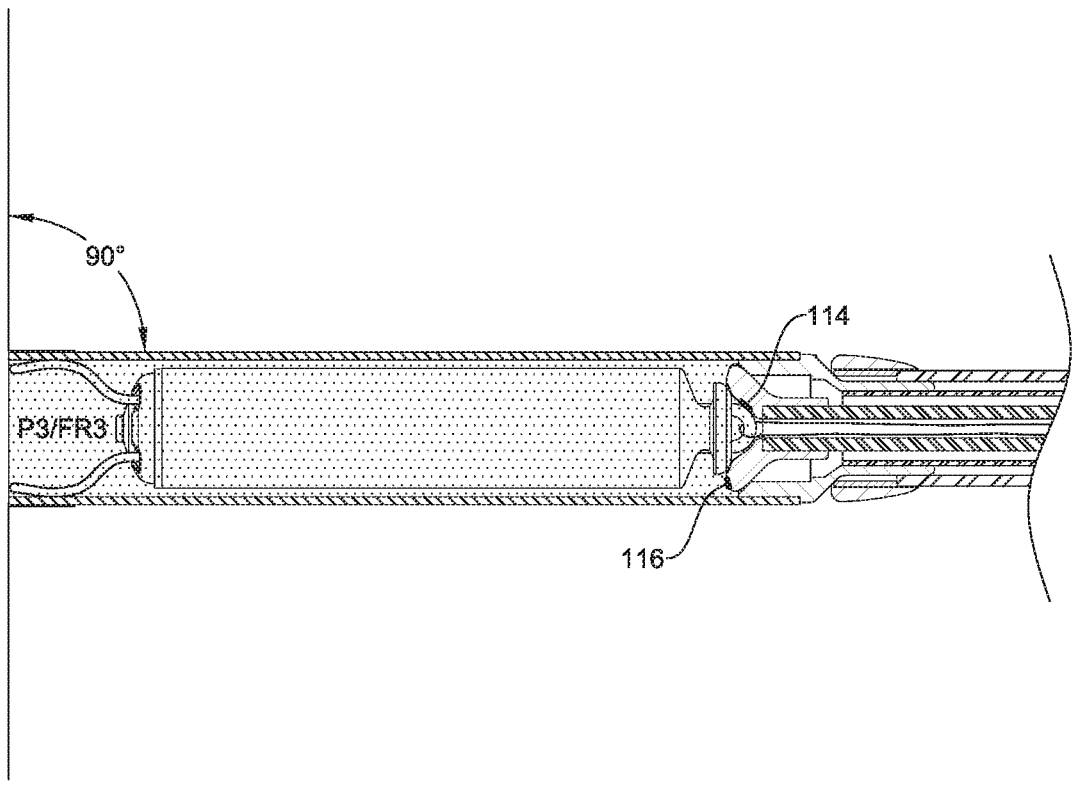

FIG. 4A illustrates an example of implementation of the flow-sensing device for deploying an implantable leadless cardiac pacing device into a chamber of a heart H, such as the right ventricle RV. As can be seen, FIG. 4A depicts a cross sectional view of the distal holding section 108 encompassing the implantable leadless cardiac pacing device 100. According to various embodiments, when the distal holding section 108 is at a target region and the distal tip portion 340 of the holding section 108 has engaged the heart wall 120, the delivery device 104 may dispense fluid through the catheter shaft 202 and into the holding section 108. As the fluid is dispensed, the flow-sensing devices 114 and 116 may detect the pressure of the fluid (i.e., P1). Additionally or alternatively, the flow-sensing devices 114 and 116 may detect the flow-rate of the fluid (i.e., FR1). In this example, a degree of wall apposition between the distal end 110 and the chamber wall 120 is high, with the longitudinal axis of the implantable device 100 substantially perpendicular to the plane of the tissue. As a result, as seen in FIG. 4B, a seal between the distal opening 112 and the chamber wall 120 is created and the fluid pressure in the cavity 118 of the distal holding section 108 rises to P2 and the fluid flow-rate in the cavity decreases to FR2 as additional fluid is delivered to the cavity 118. In certain embodiments, the flow-sensing devices 114 and 116 may be programmed with ranges of acceptable pressures that change with respect to time to account for the change in the amount of fluid within the cavity 118. Additionally or alternatively, the flow-sensing devices 114 and 116 may be programmed with ranges of acceptable flow-rates that change with respect to time to account for the change in the amount of fluid within the cavity. As seen in FIG. 4C, the fluid pressure may rise to P3, within the range of acceptable pressures and the flow-rate may decrease to FR3, within the range of acceptable flow-rates, as the fluid continues to be delivered to the cavity 118. In this example, the flow-sensing devices 114 and 116 may detect that the fluid pressure and/or the fluid flow-rate within the distal holding section 108 consistently falls within a range of acceptable pressures for each given time. Therefore, an operator can determine that the distal holding section 108 may be positioned appropriately to the chamber wall 120 and there is a likelihood that the implantable device 100 will be successfully deployed into the chamber 120 of heart H.

Figure 5:
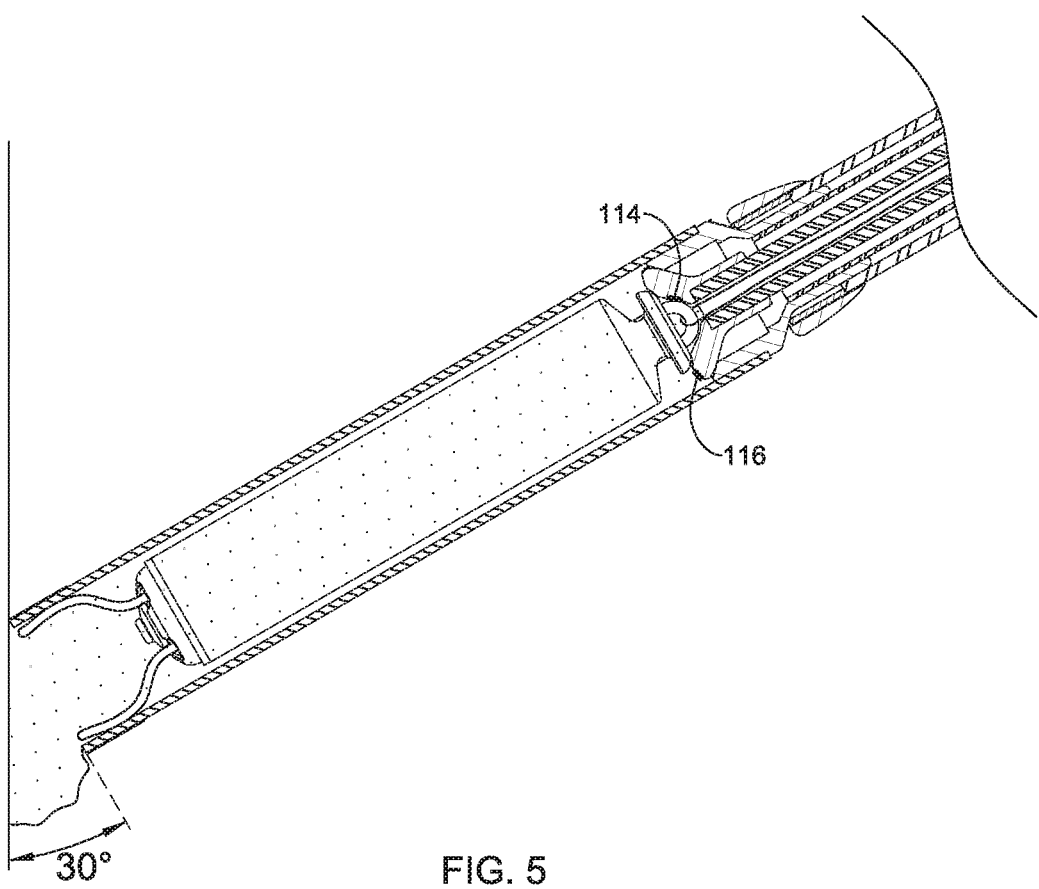
FIG. 5 illustrates an example of implementation of the pressure sensing device for deploying an implantable leadless cardiac pacing device into a chamber of a heart.

FIG. 5 illustrates another example of implementation of the flow-sensing device for deploying an implantable leadless cardiac pacing device into a chamber of a heart H, such as the right ventricle RV. As can be seen, FIG. 5 depicts a cross sectional view of the distal holding section 108 encompassing the implantable leadless cardiac pacing device 100. According to various embodiments, when the distal holding section 108 is at a target region and a distal tip portion 340 of the holding section 108 has engaged the heart wall, the delivery device may dispense fluid through the catheter shaft 202 and into the holding section 108. As the fluid is dispensed, the flow-sensing devices 114 and 116 may detect the pressure and/or the flow-rate of the fluid within the cavity 118. In this example, a degree of wall apposition between the distal end 110 and the chamber wall 120 is unacceptable. As a result, a seal does not exist between the distal opening 112 and the chamber wall 120, allowing the fluid to flow out of the distal opening 112 and thus the pressure within the cavity 118 does not increase into the acceptable range and the flow-rate within the cavity 118 does not decrease into the acceptable range. In certain embodiments, similar to the pressure analysis from FIGS. 4A-4C, the flow-sensing devices 114 and 116 may be programmed with ranges of acceptable pressures that change with respect to time to account for the change in the amount of fluid delivered to the cavity 118. Accordingly, the range of acceptable pressures may increase to account for the increase in fluid delivered. Additionally or alternatively, the flow-sensing devices 114 and 116 may be programmed with ranges of acceptable flow-rates that change with respect to time to account for the change in the amount of fluid delivered to the cavity 118. Accordingly, the range of acceptable flow-rates may decrease to account for the increase in fluid delivered. However, because of the separation between the distal end 110 and the chamber wall 120, the fluid pressure may not rise into the acceptable range of pressures and the fluid flow-rate may not decrease into the acceptable range of flow-rates. As a result, the flow-sensing devices 114 and 116 may detect that the fluid pressure within the distal holding section 108 consistently falls outside the range of acceptable pressures for each given time. Additionally or alternatively, the flow-sensing devices 114 and 116 may detect that the fluid flow-rate within the distal holding section 108 consistently falls outside the range of acceptable flow-rate for each given time. An operator may then determine that the distal holding section 108 may not be positioned appropriately to the chamber wall 120 and there is a likelihood that the implantable device 100 will not be successfully deployed into the chamber 120 of heart H. Therefore, repositioning of the distal holding section 108 may be necessary prior to deployment of the implantable device 100.

Figure 6:
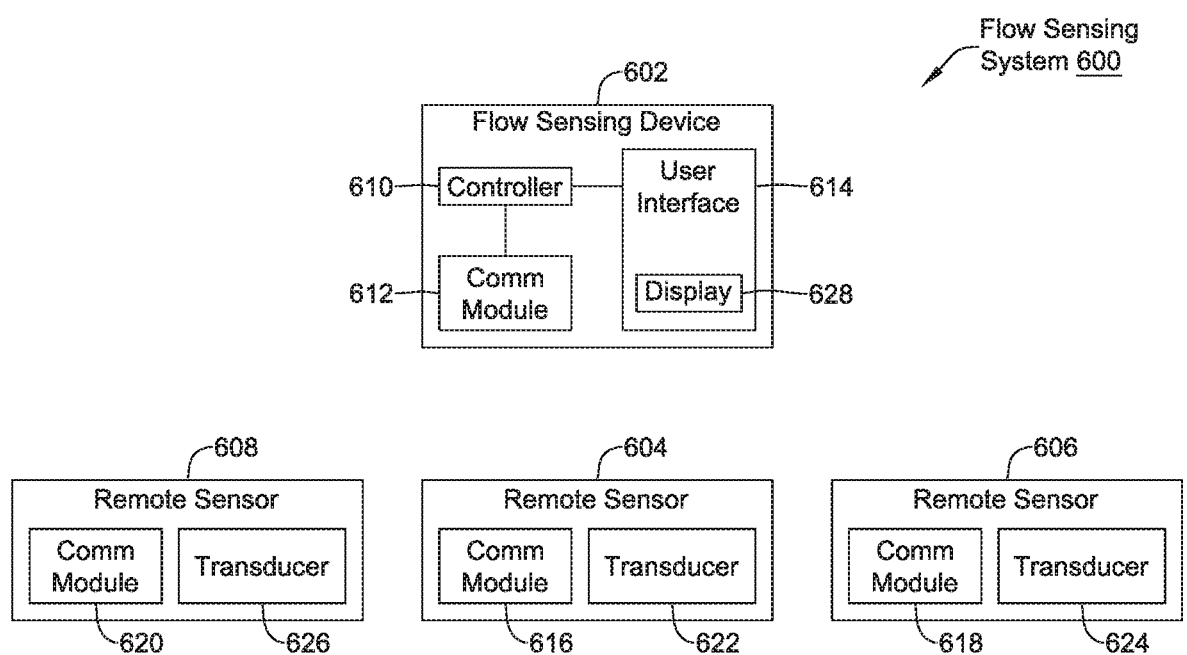
FIG. 6 depicts an illustrative pressure sensing system that may be used in conjunction with a delivery device.

FIG. 6 depicts an illustrative flow-sensing system 600 that may be used in conjunction with a delivery device to deliver an implantable leadless cardiac pacing device in a chamber of a heart H. As can be seen in FIG. 6, the flow-sensing system 600 can include a flow-sensing device 602 and remote sensors 604, 606, and 608. In some cases, the remote sensors 604, 606, and 608 may be considered as being an example of one or more of the flow-sensors (FIGS. 1-5). In the example shown in FIG. 6, the flow-sensing device 602 may include a controller 610, a communication module 612, and a user-interface 614. Furthermore, each remote sensor 604, 606, and 608 may include a communication module 616, 618, and 620 and a transducer 622, 624, and 626. The flow-sensing system 600 may include more or less remote sensors, depending on the application.

The controller 610 can be configured to control the operation of the flow-sensing system 600. For example, the controller 610 may be configured to receive electrical signals from the remote sensors 604, 606, and 608. Based on the received signals, the controller 610 may determine, for example, the pressure and/or the flow-rate of the fluid in the distal holding section 108. Based on the determined pressure and/or flow-rate, the controller 610 may control the user-interface 614 to generate a read out on a display 628 that can be observed by an operator (e.g., a physician, clinician, etc.). In some examples, the controller 610 may use information to determine whether the pressure and/or flow-rate of the fluid in the distal holding section 108 is within an acceptable range of values and present this information to the operator using the display 628.

The communication module 612 may be configured to communicate with the remote sensors 604, 606, and 608 and other electronic or mechanical systems on the delivery device 104 or other medical devices that are located externally to the flow-sensing device 602. Such devices may be located either external or internal to the patient's body. Irrespective of the location, external devices (i.e. external to the flow-sensing device 602 but not necessarily external to the patient's body) can communicate with the flow-sensing device 602 via communication module 612 to accomplish one or more desired functions. For example, the remote sensors 604, 606, and 608 may observe the pressure and/or flow-rate of the fluid in the distal holding section 108 using the transducers 622, 624, and 626. The remote sensors 604, 606, and 608 may then use the communication modules 616, 618, and 620 to send encoded communication signals as sensed electrical signals, data, instructions, messages, etc., to the communication module 612. The flow-sensing device 602 may use the encoded communicated signals to display a signal indicative of the sensed pressures and/or flow-rates on a display 628 of the user-interface 614 and/or perform any other suitable function. The communication module 612 may additionally be configured to use one or more methods for communicating with external devices, such as remote sensors 604, 606, and 608. For example, the communication module 612 may communicate via radiofrequency (RF) signals, inductive coupling, optical signals, acoustic signals, conducted communication signals, and/or any other signals suitable for communication.

According to various embodiments, when the distal holding section 108 is at a target region and the distal tip 340 of the holding section 108 has engaged the heart wall, the delivery device may dispense fluid (e.g., saline) through the catheter shaft 202 and into the holding section 108. At which time, the controller 610 may receive a signal that the pressure and/or flow-rate of the fluid in the distal holding section 108 must be read. In some embodiments, the controller 610 may receive the signal as a communication signal automatically, through the communication module 612, from a fluid dispensing system (not shown) that sends the communication signal remotely once it begins dispensing the fluid. In other embodiments, the controller 610 may receive the signal as an electrical signal from the operator, through their interaction with the user-interface 614. The controller 610 may send the signal to the communication module 612, where the communication module 612 can send pressure and/or flow-rate reading communication signals to each communication module 616, 618, and 620 of the remote sensors 604, 606, and 608 to initiate an observation of the fluid pressure and flow-rate in the distal holding section 108. The pressure and/or flow-rate reading communication signals may then be transformed into electrical signals and relayed to the transducers 622, 624, and 626. In response, the transducers 622, 624, and 626 can observe the fluid pressure and/or flow-rate and send electrical signals back to the communication modules 616, 618, and 620. In certain embodiments, the electrical signals sent back may vary depending on the change in the fluid pressure and/or glow-rate. The communication modules 616, 618, and 620 can encode these varying electrical signals into communication signals that preserve both the information of the varying electrical signals and the remote sensor that sent the varying electrical signal. The communication modules 616, 618, and 620 may then send the encoded communication signals to the communication module 612, where it is transformed back into an electrical signal and relayed to the controller 610. The controller 610 may then interpret the electrical signal to determine the fluid pressure and/or flow-rate and use the user-interface 614 to generate a read-out indicative of the fluid pressure and/or flow-rate on the display 628.

The fluid pressure and/or flow-rate read-out may have multiple embodiments and configurations. Furthermore, multiple read-out embodiments may be present on a single read-out. For example, the fluid pressure and/or flow-rate read-out can be a visual chart where a range of pressure and/or flow-rate values are displayed. This range of pressure and/or flow-rate values can indicate a region that the fluid pressure and/or flow-rate must lie within to indicate that the distal end 110 is positioned acceptably adjacent to the chamber wall 120 to create a seal between the distal opening 112 and the chamber wall 120. If an indication of the pressure and/or flow-rate value lies within the region of acceptable pressure and/or flow-rate values, the operator can determine that the distal holding section 108 may be positioned appropriately to the chamber wall, thus, increasing the likelihood of acceptable deployment of the implantable device. For example, a fluid pressure between 10 mmHg and 150 mmHg may indicate that the distal holding section 108 is positioned acceptably adjacent to the chamber wall 120. The read-out on the display 628 shows that the fluid pressure in the distal holding section 108 is within the acceptable range as it varies between 124 mmHg and 127 mmHg, for example. Therefore, an operator can determine that successful deployment of the implantable device is likely. Additionally or alternatively, a flow-rate between 1.5 mL/s to 4 mL/s may indicate that the distal holding section 108 is positioned acceptably adjacent to the chamber wall 120. The read-out on the display 628 shows that the fluid flow-rate in the distal holding section 108 is within the acceptable range as it varies between 3.25 mL/s and 3.3 mL/s, for example. Therefore, an operator can determine that successful deployment of the implantable device is likely.

If, however, the indication of the pressure and/or flow-rate value is not within the region of acceptable pressure and/or flow-rate values, the operator can determine that the distal holding section 108 may not be positioned appropriately to the chamber wall 120, and the distal holding section 108 must be repositioned and the deployment positon analysis can begin again. For example, the read-out on the display 628 may show an indication that the fluid pressure in the distal holding section 108 is not within the 10-150 mmHg range, as it varies between 4 mmHg and 6 mmHg, for example. Therefore, an operator can determine that a seal has not been created between the distal opening 112 and the chamber wall 120. The operator may then use the delivery device 104 to reposition the distal holding section 108 to the target region of the chamber wall 120. When the distal holding section 108 is at the target region, pressure analysis can begin and a new read-out can be generated on the display 628. This time, the read-out on the display 628 shows an indication that the fluid pressure in the distal holding section 108 is within the 10-150 mmHg range as it varies between 112 mmHg and 116 mmHg, for example. Therefore, an operator can determine that successful deployment of the implantable device is likely.

Additionally or alternatively, the read-out on the display 628 may show an indication that the fluid flow-rate in the distal holding section 108 is not within the 1.5-4 mils range, as it varies between 5 and 5.3 mils, for example. Therefore, an operator can determine that a seal has not been created between the distal opening 112 and the chamber wall 120. The operator may then use the delivery device 104 to reposition the distal holding section 108 to the target region of the chamber wall 120. When the distal holding section 108 is at the target region, flow-rate analysis can begin and a new read-out can be generated on the display 628. This time, the read-out on the display 628 shows an indication that the fluid flow-rate in the distal holding section 108 is within the 1.5-4 mL/s range as it varies between 2.6 and 2.9 mL/s, for example. Therefore, an operator can determine that successful deployment of the implantable device is likely.

In another embodiment, the fluid pressure and/or flow-rate read-out can display a numerical value of the fluid pressure. The operator may know beforehand an acceptable range of values that the fluid pressure and/or flow-rate must have to indicate that the distal end 110 is positioned acceptably adjacent to the chamber wall 120. If the pressure and/or flow-rate value is within the known range, the operator can determine that the distal holding section 108 may be positioned appropriately to the chamber wall, thus, increasing the likelihood of acceptable deployment of the implantable device 100. If, however, the pressure and/or flow-rate value is not within the acceptable range, the operator can determine that the distal holding section 108 may not be positioned appropriately to the chamber wall, and the distal holding section 108 must be repositioned and the deployment positon analysis can begin again.

In another embodiment, the user-interface 614 may also include illuminating devices, such as LED's, or audio devices, such as speakers, to signal whether the fluid pressure is acceptable or unacceptable. For example, the controller 610 may be given an acceptable range of values that the fluid pressure and/or the flow-rate must have to indicate the distal end 110 is positioned acceptably adjacent to the chamber wall 120. Once the controller 610 determines the fluid pressure and/or flow-rate, the controller 610 may then compare the fluid pressure and/or flow-rate to the acceptable range of values. If the pressure and/or flow-rate value is within the acceptable range, the controller 610 can use the illuminating devices or audio device, to inform the operator that the fluid pressure and/or flow-rate is acceptable, thus, increasing the likelihood of acceptable deployment of the implantable device. For example, the controller 610 determines that the fluid pressure varies between 124 mmHg and 127 mmHg. The controller 610 then sends instructions to the user-interface 614 to generate the visual chart read-out on the display 628 and/or turn on a green LED (not shown) signaling to the operator that the fluid pressure is within the acceptable range. Additionally or alternatively, the controller 610 may determine that the fluid flow-rate varies between 2.6 mL/s and 2.8 mL/s. The controller 610 then sends instructions to the user-interface 614 to generate the visual chart read-out on the display 628 and/or turn on a green LED (not shown) signaling to the operator that the fluid flow-rate is within the acceptable range.

If, however, the controller 610 determines the pressure and/or flow-rate value is not within the acceptable range, the controller 610 can use or not use the illuminating devices or audio devices, to tell the operator that the fluid pressure and/or flow-rate is unacceptable. The operator may then determine that the distal holding section 108 must be repositioned and the deployment positon analysis can begin again. For example, the controller 610 determines that the fluid pressure varies between 4 mmHg and 6 mmHg. The controller 610 then sends instructions to the user-interface 614 to generate the visual chart read-out on the display 628 and turn on a red LED (not shown) signaling to the operator that the fluid pressure is not within the acceptable range. Additionally or alternatively, the controller 610 may determine that the fluid flow-rate varies between 5 mL/s and 5.2 mL/s 4 mmHg and 6 mmHg. The controller 610 then sends instructions to the user-interface 614 to generate the visual chart read-out on the display 628 and turn on a red LED (not shown) signaling to the operator that the fluid pressure is not within the acceptable range.

Figure 7:
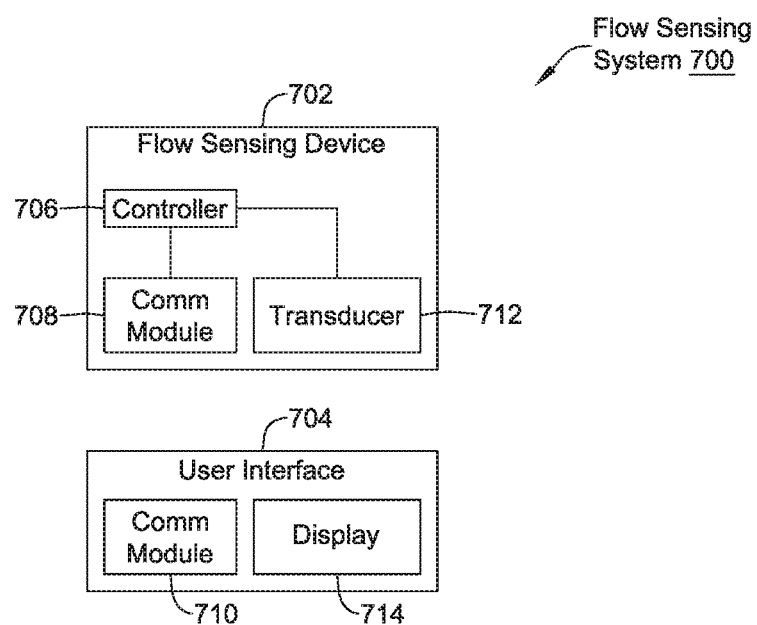
FIG. 7 depicts an illustrative pressure sensing system that may be used in conjunction with a delivery device.

FIG. 7 depicts another illustrative flow-sensing system 700 that may be used in conjunction with a delivery device to deliver an implantable leadless cardiac pacing device in a chamber of a heart H. As can be seen in FIG. 7, the flow-sensing system 700 can include a flow-sensing device 702 and a remote user-interface 704. In some cases, the flow-sensing device 702 may be considered as being an example of one or more of the flow-sensing devices (FIGS. 1-5). In the example shown in FIG. 7, the flow-sensing device 702 may include a controller 706, a communication module 708, and a transducer 712. Furthermore, the remote user-interface 704 may include a communication module 710 and a display 714.

According to various embodiments, the pressure flow-sensing device 702 can operate similar to the pressure sensing device 602, depicted in FIG. 6. However, in the example shown in FIG. 7, the flow-sensing device 702 is configured to incorporate the transducer 712 and is capable of observing the pressure and/or the flow-rate of the fluid in the distal holding section 108 without interacting with remote sensors through wired or wireless communication.

For example, when the distal holding section 108 is at a target region and a distal tip portion 110 of the holding section 108 has engaged the heart wall, the delivery device 104 may dispense fluid through the catheter shaft 202 and into the distal holding, section 108. At which time the controller 706 may receive a signal that the pressure and/or flow-rate of the fluid in the distal holding section 108 must be read. Similar to the flow-sensing system 600, in some embodiments, the controller 702 may receive the signal as a communication signal automatically, through the communication module 708, from a fluid dispensing system (not shown) that sends the communication signal remotely once it begins dispensing the fluid. In other embodiments, the controller 706 may receive the signal as a communication signal from the operator, through their interaction with the remote user-interface 704. The controller 706 may then relay the signal to the transducer 712. In response, the transducer 712 can Observe the fluid pressure and/or the flow-rate and send an electrical signal back to the controller 706. In certain embodiments, the electrical signal sent back may vary depending on the change in the fluid pressure and/or flow-rate. The controller 706 may then interpret the electrical signal to determine the fluid pressure and/or flow-rate and generate an electrical signal encoded with the determined fluid pressure and/or flow-rate and instructions for generating a read-out of the fluid pressure and/or flow-rate on the display 714. The electrical signal is then relayed to the communication module 708 where the communication module 708 can transform the electric signal into a communication signal and send it to the communication module 710 of the user-interface 704. The communication module 710 may then transform the communication signal back into an electric signal and relay it to the display 714 to generate a read-out of the fluid pressure and/or flow-rate.

Similar to the pressure sensing system 600 of FIG. 6, the fluid pressure and/or flow-rate read-out may have multiple embodiments and configurations and multiple read-out embodiments may be present on a single read-out. Furthermore, the number of read-outs and their configuration may be determined by the preferences of the operator.

Figure 8:
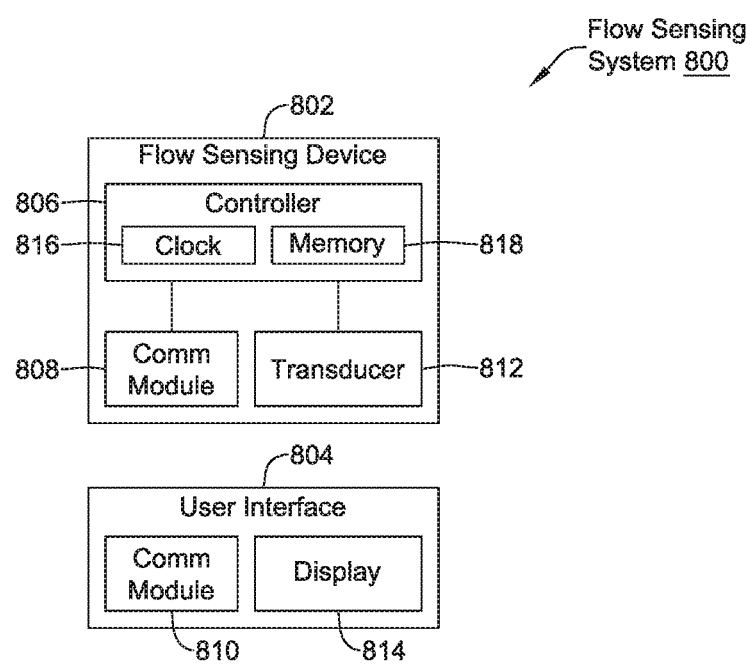
FIG. 8 depicts an illustrative pressure sensing system that may be used in conjunction with a delivery device.

FIG. 8 depicts another illustrative flow-sensing system 800 that may be used in conjunction with a delivery device to deliver an implantable leadless cardiac pacing device in a chamber of a heart H. As can be seen in FIG. 8, the flow-sensing system 800 can include a flow-sensing device 802 and a remote user-interface 804. In some cases, the flow-sensing device 802 may be considered as being an example of one or more of the flow-sensing devices (FIGS. 1-5). In the example shown in FIG. 8, the flow-sensing device 802 may include a controller 806, a communication module 808, and a transducer 812. Furthermore, the remote user-interface 804 may include a communication module 810 and a display 814.

In some examples, the controller 806 may include a pre-programmed chip, such as a very-large-scale integration (VLSI) chip and/or an application specific integrated circuit (ASIC). In such embodiments, the chip may be pre-programmed with control logic in order to control the operation of the pressure sensing system 800. By using a pre-programmed chip, the controller 806 may use less power than other programmable circuits (e.g. general purpose programmable microprocessors) while still being able to maintain basic functionality, thereby potentially increasing the battery life of the pressure sensing device 802. In other examples, the controller 806 may include a programmable microprocessor. Such a programmable microprocessor may allow a user to modify the control logic of the pressure sensing system 800 even after implantation, thereby allowing for greater flexibility of the pressure sensing system 800 than when using a pre-programmed ASIC. In some examples, the controller 806 may further include a memory 818, and the controller 806 may store information on and read information from the memory 818. In other examples, the controller 806 may include a remote memory (not shown) that is in communication with the controller 806 through the communication module 808, such that the controller 806 may read and write information to and from the remote memory. In yet further examples, the controller 806 may also include a clock 816, and the controller 806 may record a time using the clock 816 and store the time record in the memory 818 or in the remote memory.

In some examples, regardless of whether the controller includes a pre-programmed chip or a programmable microprocessor, the controller may be programmed with interrupt logic. An interrupt can alert the controller 806 to a high-priority condition requiring the interruption of the current code the controller 806 is executing. The controller 806 responds by suspending its current activities, saving its state, and executing a function called an interrupt handler (or an interrupt service routine, ISR) to deal with the event. This interruption is temporary, and, after the interrupt handler finishes, the controller 806 can resume normal activities. Hardware interrupts can be used by devices, such as the user-interface 804, a fluid dispensing system (not shown), or another medical device. Internally, the hardware interrupts can be implemented using electronic alerting signals that are sent from the user-interface 804 the fluid dispensing system, or another medical device to the controller 806.

For example, when the distal holding section 108 is at a target region and a distal tip portion 340 of the holding section 108 has engaged the heart wall 120, a fluid dispensing system may dispense fluid through a catheter shaft 202 and into the holding section 108. If the distal end 110 is positioned acceptably adjacent to the chamber wall 120, a seal should be created between the circumference of the distal opening 1 and the chamber wall 120. As the fluid is dispensed, the fluid pressure should rise given that the fluid is unable to flow out of the distal opening 112 because of the seal. Therefore, in this embodiment, the controller 806 may be programmed to detect the fluid pressure for a given dispensing time period. Additionally or alternatively, as the fluid is dispensed, the fluid flow-rate should decrease given that the fluid is unable to flow out of the distal opening 112 because of the seal. Therefore, in this embodiment, the controller 806 may be programmed to detect the fluid flow-rate for a given dispensing time period. During the dispensing period, the controller 806 is programmed with a range of acceptable fluid pressures and/or flow-rate that vary with respect to time. Each range of acceptable fluid pressures and/or flow-rates may indicate a range of acceptable pressure and/or flow-rate values the fluid can have at that specific time.

In addition, the controller 806 may receive an interrupt signal through the communication module 808 from the fluid dispensing system. The controller 806 may interpret this interrupt signal as an indication that the fluid dispensing system has begun dispensing fluid into the distal holding section 108 and the fluid pressure and/or flow-rate must be determined. In response, the controller 806 triggers the dock 816 to run for the programmed dispensing time and triggers the transducer 812 to observe the fluid pressure and/or flow-rate within the distal holding section 108. The transducer then relays its observation back to the controller 806 and the clock relays the time back to the controller 806. The controller 806 may then compare the measured fluid pressure and/or flow-rates against the range of acceptable pressures and/or flow-rates for that given time. The controller 806 may then use communication modules 808 and 810 to transfer the fluid pressure and/or flow-rate results to the user-interface 804 to generate a read-out on the display 814. For example, the controller 806 is programmed that a fluid pressure should be between 10 mmHg and 75 mmHg, 2 seconds into the dispensing time, to indicate the distal holding section 108 is positioned acceptably adjacent to the chamber wall 120. The controller 806 may then determine that the current fluid pressure at 2 seconds is 6 mmHg and generates the visual chart read-out on the display 818.

Continuing with the current example, the controller 806 may also be programmed that a fluid pressure should be between 10 mmHg and 150 mmHg, 4 seconds into the dispensing time, to indicate the distal holding section 108 is positioned acceptably adjacent to the chamber wall. The controller 806 may then determine that the current fluid pressure at 4 seconds is still 6 mmHg and generates the visual chart read-out on the display 818. Therefore, an operator can determine that a seal has not been created between the distal opening 112 and the chamber wall 120 and repositioning of the distal holding section 108 may be necessary.

Additionally or alternatively, in another example, the controller 806 is programmed that a fluid flow-rate should be between 3 mL/s and 4 mL/s, 2 seconds into the dispensing time, to indicate the distal holding; section 108 is positioned acceptably adjacent to the chamber wall 120. The controller 806 may then determine that the current fluid pressure at 2 seconds is 3.3 mils and generates the visual chart read-out on the display 818. Continuing with the current example, the controller 806 may also be programmed that a fluid flow-rate should be between 1.5 mils and 3 mL/s, 4 seconds into the dispensing time, to indicate the distal holding section 108 is positioned acceptably adjacent to the chamber wall. The controller 806 may then determine that the current fluid pressure at 4 seconds is still 3.5 mL/s and generates the visual chart read-out on the display 818. Therefore, an operator can determine that a seal has not been created between the distal opening 112 and the chamber wall 120 and repositioning of the distal holding section 108 may be necessary.

Similar to the flow-sensing system 600 of FIG. 6 and system 700 of FIG. 7, the fluid pressure and/or flow-rate read-out may have multiple embodiments and configurations and multiple read-out embodiments may be present on a single read-out. Furthermore, the number of read-outs and their configuration may be determined by the preferences of the operator.

Figure 9A:
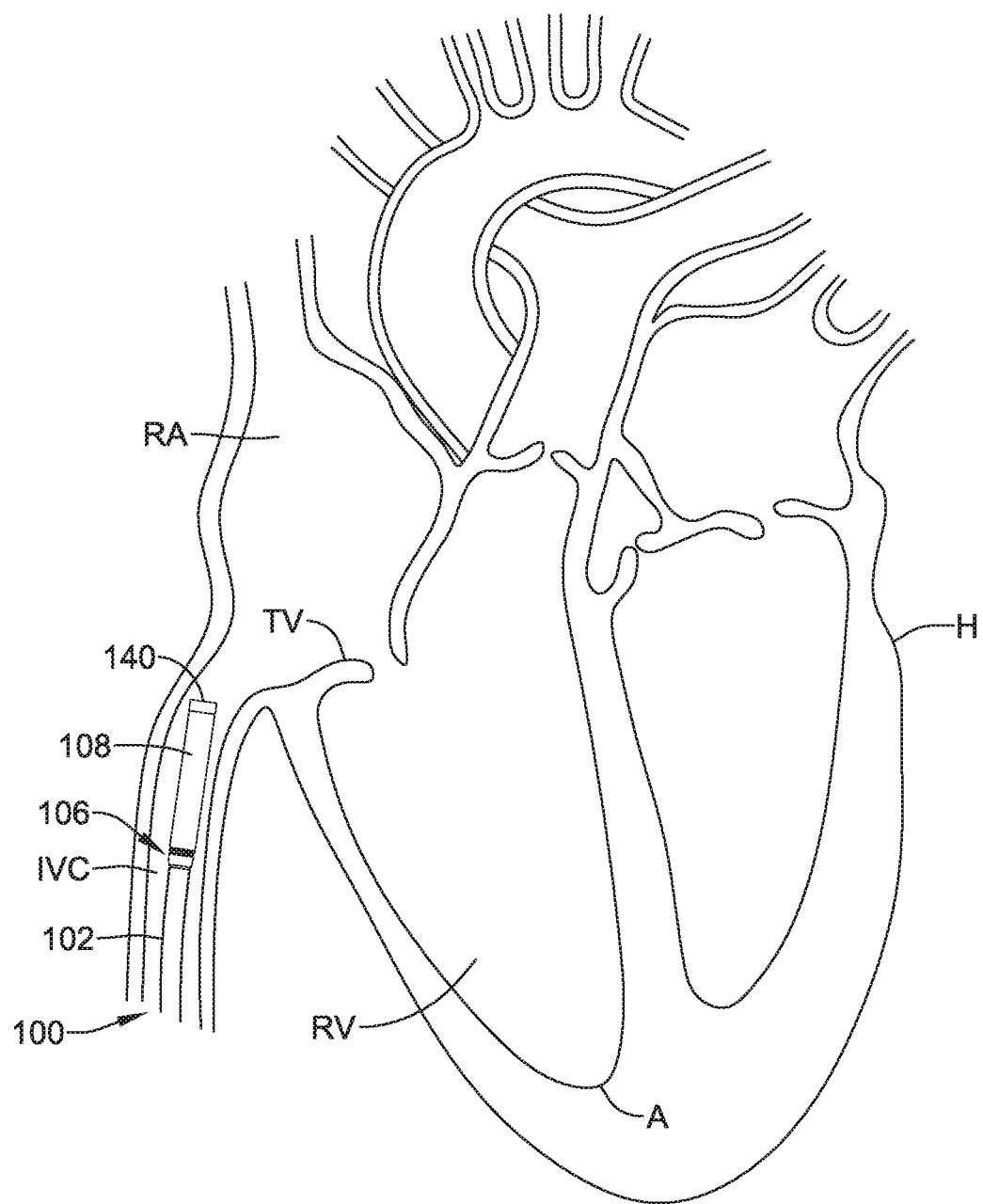
FIGS. 9A-9D depict an exemplary method for deploying a device using a delivery device.

Referring now to FIGS. 9A-9D, an exemplary method for deploying a device 100 using the illustrative delivery device 104 will now be described with respect to the distal section and distal holding section 108. The delivery device 104 may be introduced into the vasculature through the femoral vein through a previously introduced guide catheter (not explicitly shown). The delivery device 104 may be introduced through any desired location and with or without the use of a guide catheter as desired. The delivery device 104 may be advanced through the vasculature to the desired treatment location, which, in the case of the leadless cardiac pacing device 100, may be a chamber 120 of the heart H. For example, the delivery device 104 may be advanced through the vasculature to the inferior vena cava IVC, as shown in FIG. 9A, and into the right atrium RA. The operator may use an actuation mechanism to deflect the distal end portion 208 in a desired manner to facilitate advancement and/or placement of the delivery device 104. The delivery device 104 can be imaged using known techniques to ensure accurate placement of the device 100.

Figure 9B:
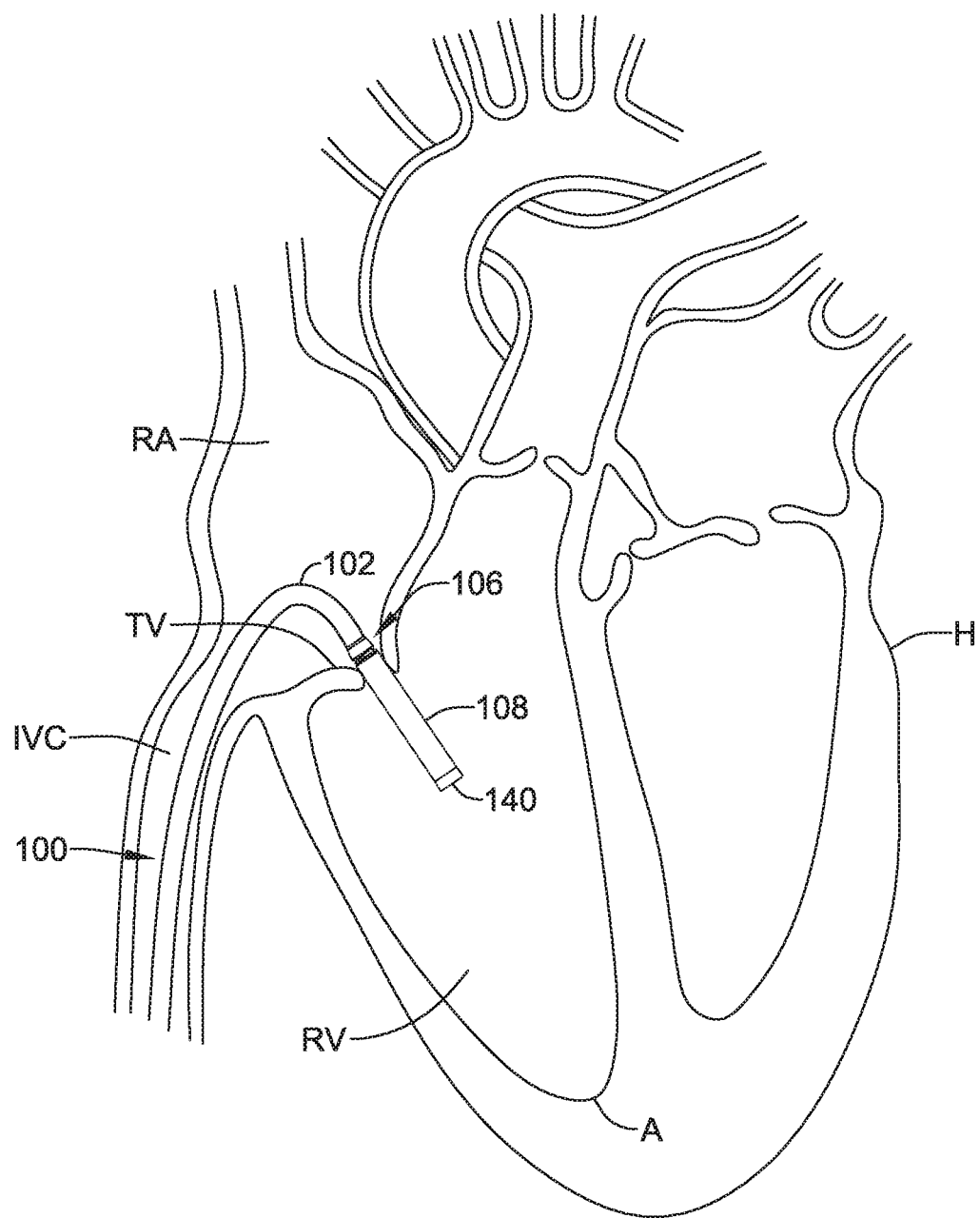
Figure 9C:
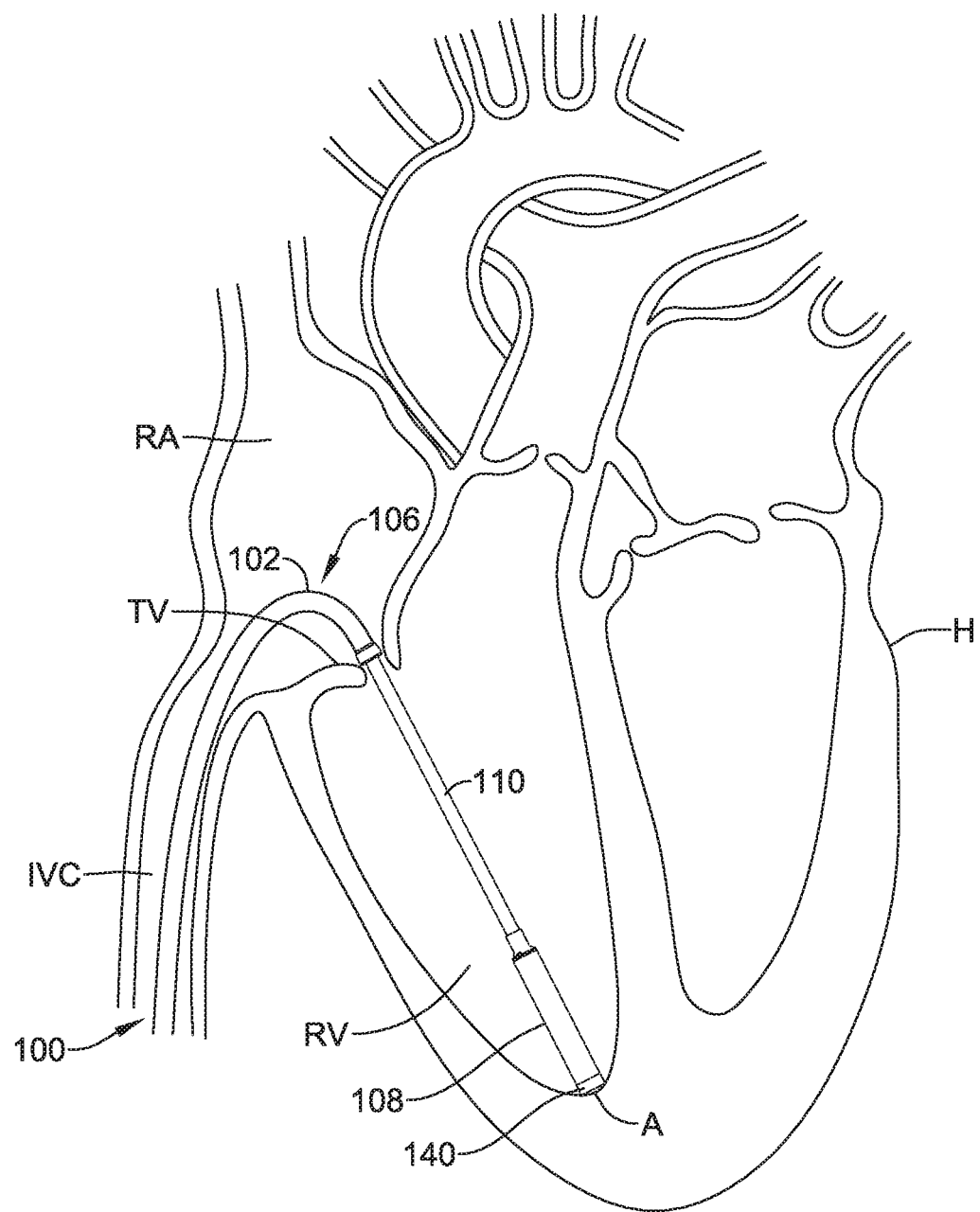

As the distal tip portion 340 of the distal holding section 108 enters the junction of the inferior vena cava IVC and the right atrium RA, the operator may use a combination of catheter manipulation (e.g. sweeping, rotating, etc.) and deflection to locate the tricuspid valve TV. Once the tricuspid valve TV has been located, the operator may further advance and/or deflect the delivery device 104 to advance the distal holding section 108 into the right ventricle RV, as shown in FIG. 9B.

Once the distal holding section 108 has been advanced across the tricuspid valve TV and into the right ventricle RV, the operator may continue to advance the distal holding section 108 to a target region A of the right ventricle RV. An average heart may have an average distance of approximately 7.5 centimeters between the tricuspid valve TV and an apex A of the right ventricle RV. In some instances, the distance between the tricuspid valve TV and the apex A of the right ventricle RV may be in the range of 4 to 12 centimeters or in the range of 6 to 10 centimeters. In a smaller heart, it may be possible for a portion of the distal holding section 108 to remain in the right atrium RA while in a larger heart the distal holding section 108 may need to be fully advanced into the right ventricle RV. For example, the distal holding portion 108 may have a length in the range of 3.5 to 5.5 centimeters or in the range of 4.0 to 5.0 centimeters.

In some instances, the distal tip portion 340 may be placed in contact with the apex A of the right ventricle RV. The delivery device 104 may dispense fluid (e.g., saline) through the catheter shaft 202 and into the holding section 108. As the fluid is dispensed, the flow-sensors 114 and 116 may detect the pressure and/or flow-rate of the fluid within the cavity 118 of the distal holding section 108. In this example, a degree of wall apposition between the distal end 110 and the chamber wall 120 is acceptable. As a result, a seal between the distal opening 112 and the chamber wall 120 is created and the fluid pressure increases in the cavity 118 of the distal holding section 108 and the fluid flow-rate decreases in the cavity 118. In certain embodiments, the flow-sensing devices 114 and 116 may be programmed with ranges of acceptable pressures and/or flow-rates that change with respect to time to account for the change in the amount of fluid delivered to the cavity 118. Accordingly, the range of acceptable pressures may increase and the range of acceptable flow-rates may decrease as the fluid continues to be delivered to the distal holding section 108. In this example, the flow-sensing devices 114 and 116 may detect that the fluid pressure and/or flow-rate within the distal holding section 108 consistently falls within a range of acceptable pressures and/or flow-rates for each given time. Therefore, the operator can determine that the distal holding section 108 may be positioned appropriately to the chamber wall 120 and there is a likelihood that the implantable device 100 will be successfully deployed into the chamber 120 of heart H.

In some embodiments, the location of the distal tip portion 340 may also be confirmed with contrast media and imaging. For example, contrast confirmation may be used to confirm the distal tip portion 340 is engaged with a wall 120 of the heart H prior to deploying the implantable device 100. It is contemplated that a flexible material may buckle or flex with an applied force (e.g. from the operator) when the distal tip portion 340 is in contact with the wall 120 of the heart H. This may provide additional confirmation under imaging that the distal tip portion 340 is engaged with the wall 120 of the heart H.

Figure 9D:
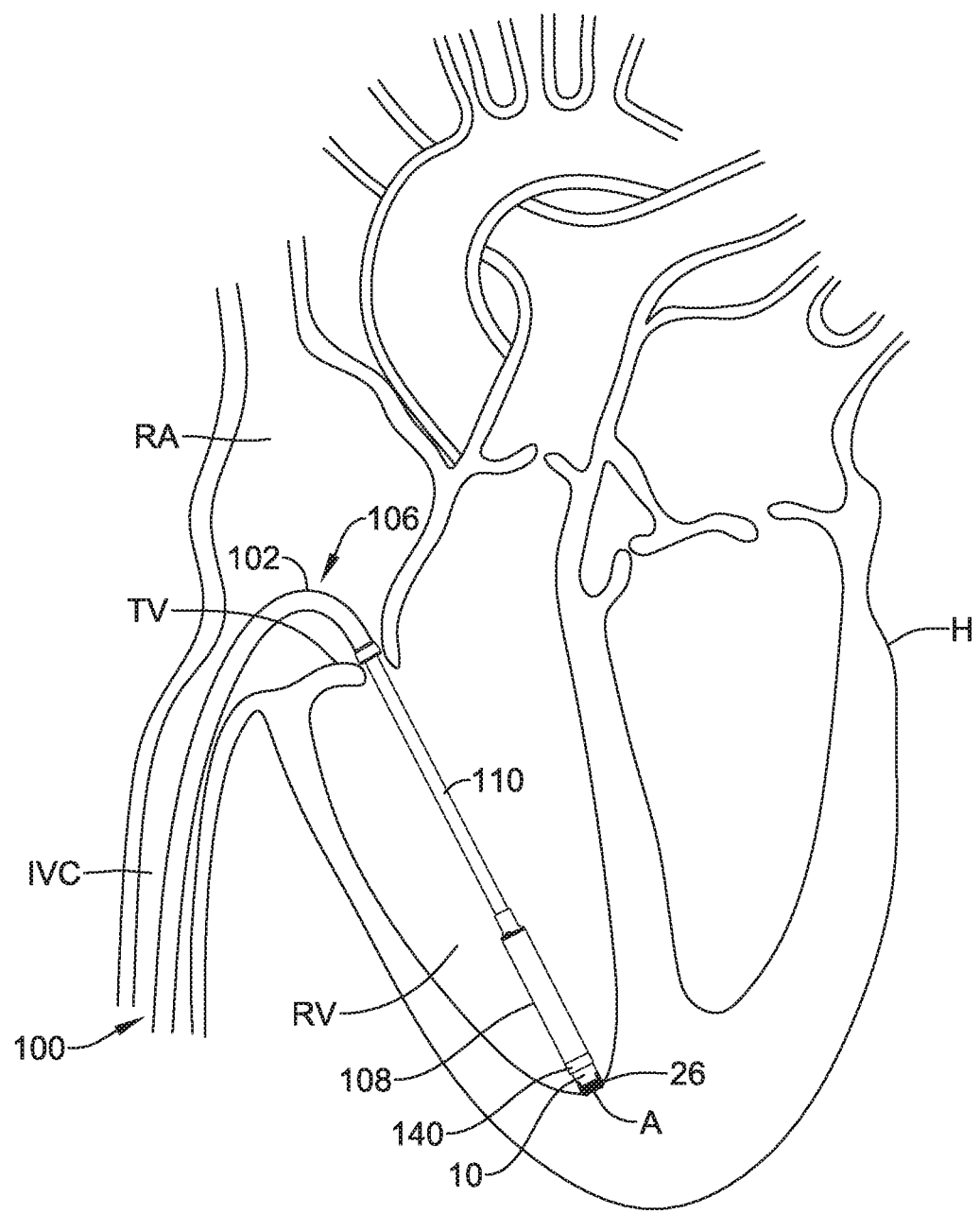

Once the distal tip portion 340 of the distal holding section 108 has been positioned adjacent to the cardiac tissue where the device 100 is desired, deployment of the device 100 can begin. The device 100 may be distally advanced out of the distal holding section 108 to deploy the hooks or tines 124, 126 from the distal holding section 108 to engage the hooks or tines 124, 126 in the heart tissue while the proximal portion of the device 100 remains within the distal holding section 108, as shown in FIG. 9D. Once the operator has determined that the position of the device 100 is satisfactory and the hooks or tines 124, 126 is securely engaged with the heart tissue, the delivery device 104, including the distal holding section 108, can be proximally retracted.

Figure 10A:
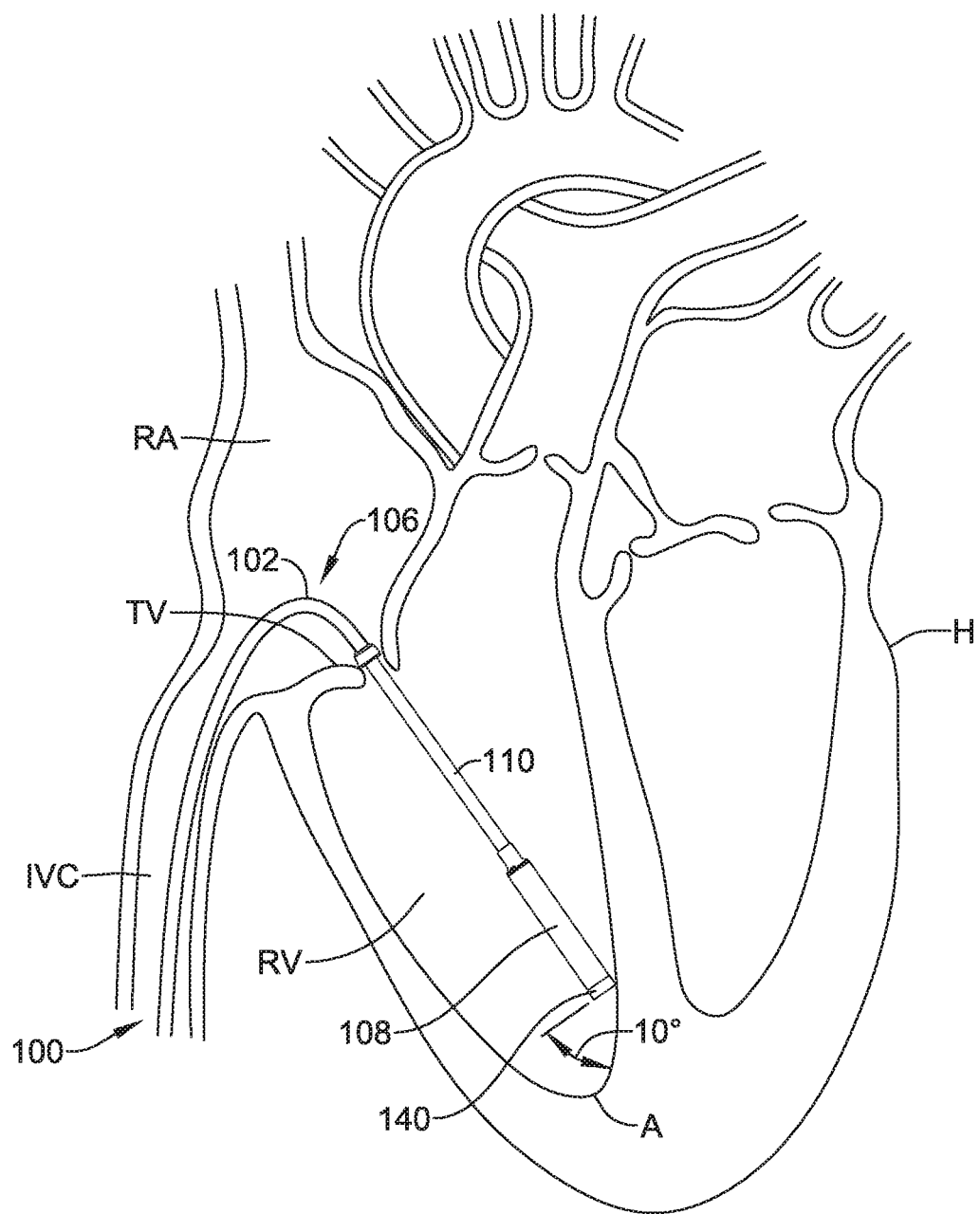
FIGS. 10A-10D depict an exemplary method for deploying a device using a delivery device.
Figure 10B:
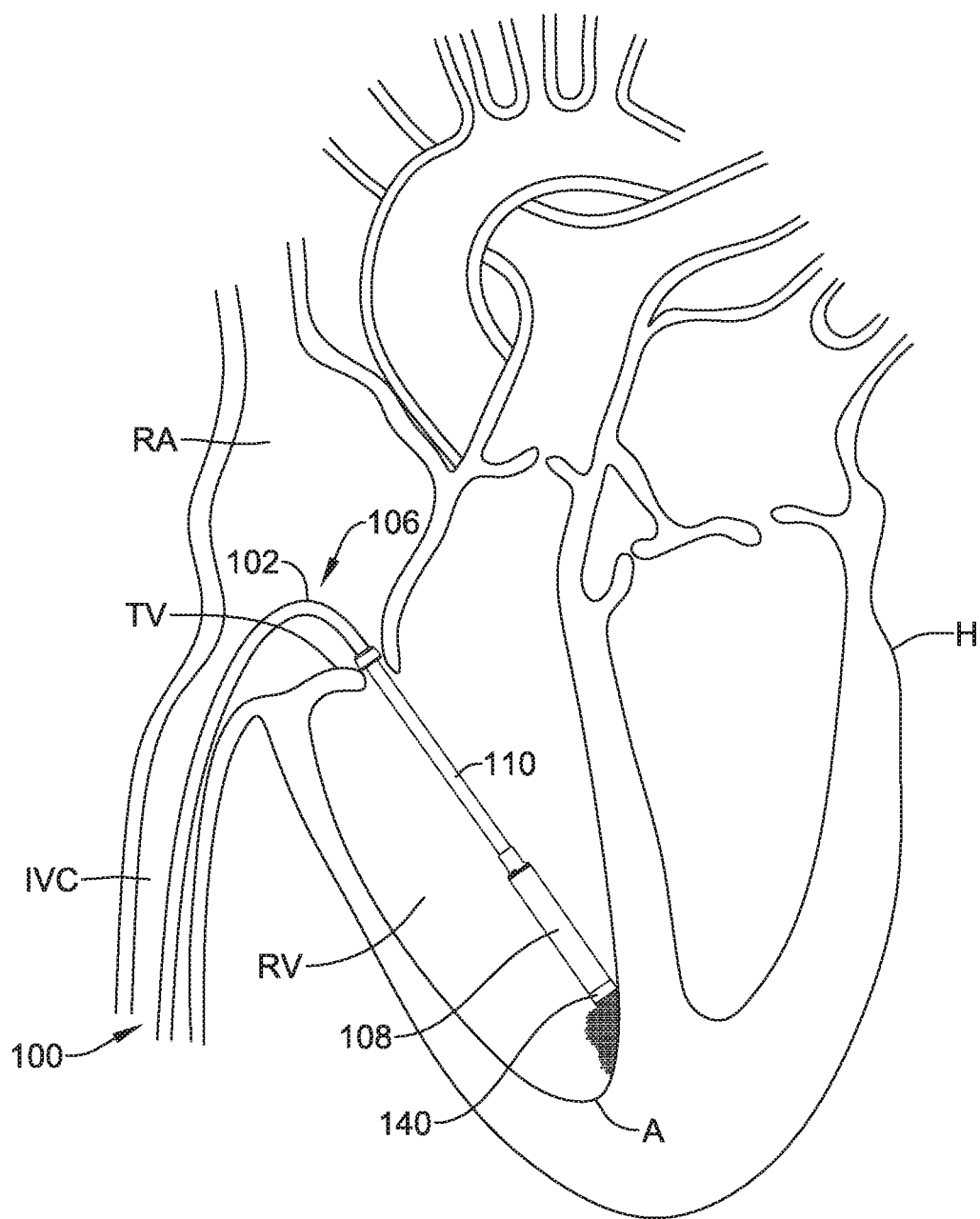
Figure 10C:
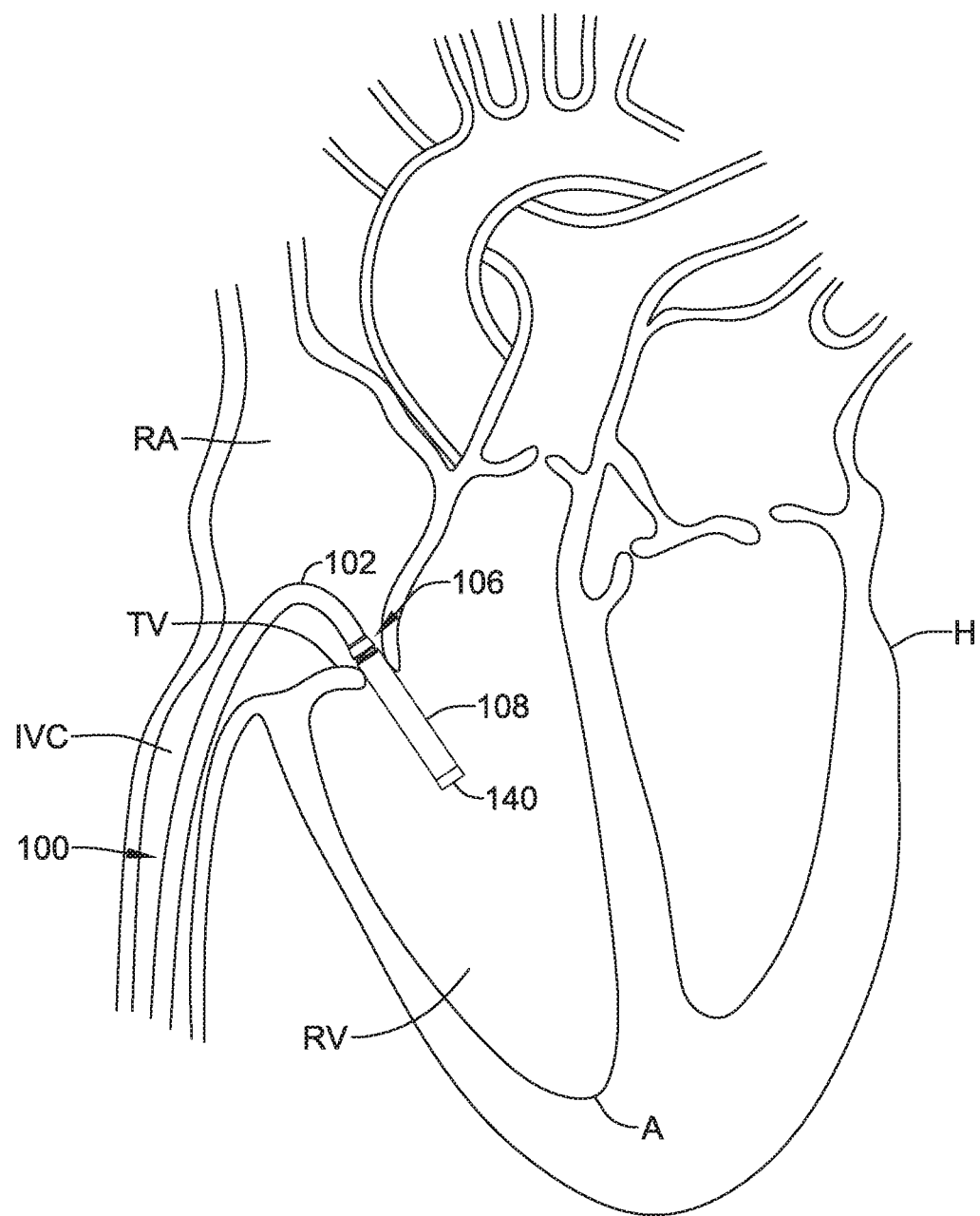
Figure 10D:
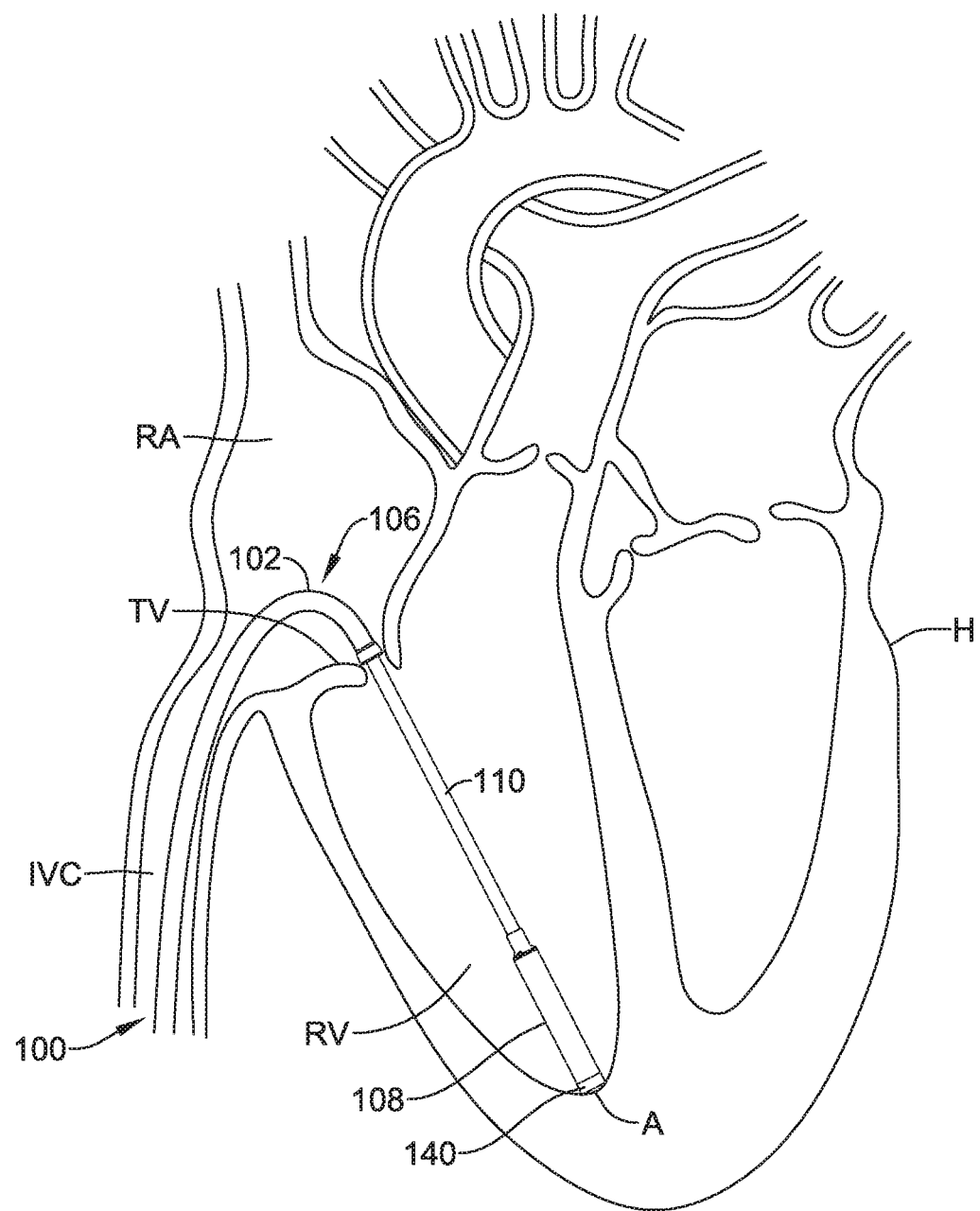

Referring now to FIGS. 10A-10D, an exemplary method for deploying a device 100 using the illustrative delivery device 104 will now be described with respect to the distal section and distal holding section 108. The method can reach the apex A of the right ventricle RV, similar to the method described in FIGS. 9A-9B. In this example, however, the distal tip portion 340 may be placed in contact with the apex A of the right ventricle RV such that, there is a 10° angle between the distal end 110 and the chamber wall 120, providing a gap between the distal end 110 and the chamber wall 120, as shown in FIG 10A. As a result, a seal does not exist between the circumference of the distal opening 112 and the chamber wall 120, allowing the fluid to flow out of the distal opening 112, as shown in FIG 10B. Fluid may then be dispensed through the catheter shaft 202 and into the cavity 118 of the holding section 108. In certain embodiments, similar to the pressure and flow-rate analysis from FIGS. 9A-9C, the flow-sensing devices 114 and 116 may be programmed with ranges of acceptable pressures and/or flow-rates that change with respect to time to account for the change in the amount of fluid within the cavity 118. However, because of the 10° angle of separation (e.g., gap) between the distal end 110 and the chamber wall 120, the fluid pressure may not rise fast enough into the acceptable range or may not rise into the acceptable range at all. Additionally or alternatively, the fluid flow-rate may not decrease fast enough into the acceptable range or may not decrease into the acceptable range at all. As a result, the flow-sensing devices 114 and 116 may detect that the fluid pressure and/or flow-rate within the cavity 118 of the distal holding section 108 consistently falls outside a range of acceptable pressures and/or flow-rates for each given time. An operator may then determine that the distal holding section 108 may not be positioned appropriately to the chamber wall 120 and there is a likelihood that the implantable device 100 will not be successfully deployed into the chamber 120 of heart H. Therefore, repositioning of the distal holding section 108 may be necessary, as shown in FIGS. 10C and 10D.

Once the flow-sensing devices 114 and 116 have sensed a pressure and/or flow-rate within the acceptable range, the operator may actuate the delivery device 104 to deploy the implantable device 100 from the distal holding section 108. As the implantable device 100 is expelled from the distal holding section 108, the hooks or tines 126 may penetrate into the tissue wall to secure the implantable device 100 to the heart wall. An acceptable pressure and/or flow rate within the acceptable pressure and/or flow-rate range may be indicative that all of or a sufficient number of the hooks or tines 126 will penetrate into the tissue wall to sufficiently secure the implantable device 100 to the heart wall.

The materials that can be used for the various components of the delivery devices, such as delivery device 104 (and/or other delivery structures disclosed herein) and the various members disclosed herein may include those commonly associated with medical devices. For simplicity purposes, the following discussion makes reference to the delivery device 104 and components of thereof. However, this is not intended to limit the devices and methods described herein, as the discussion may be applied to other similar delivery systems and/or components of delivery systems or devices disclosed herein.

The delivery device 104 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 104 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 104 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 104 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery catheter for delivering an implantable leadless pacing device, the delivery catheter comprising:
   a catheter shaft extending from a proximal end to a distal end thereof, the catheter shaft including a distal holding section defining a cavity therein for receiving the implantable leadless pacing device;
   a flow-sensing device having operational circuitry configured to determine a pressure or flow-rate of a fluid delivered into the cavity of the distal holding section through the catheter shaft while an implantable leadless pacing device is present in the cavity;
   wherein the operational circuitry of the flow-sensing device is configured to:
      send a first signal to a user indicative of an acceptable deployment location for deployment of the implantable leadless pacing device; and
      send a second signal to a user indicative of an unacceptable deployment location for deployment of the implantable leadless pacing device;
   a handle assembly including at least a hub portion affixed adjacent to the proximal end of the catheter shaft; and
   a deployment mechanism disposed within the handle assembly;
   wherein the deployment mechanism is configured to deploy the implantable leadless pacing device.

2. The delivery catheter of claim 1, wherein the flow-sensing device is operationally coupled to a user interface having a display and the operational circuitry of the flow-sensing device is further configured to:
   send the pressure or flow-rate to the display.

3. The delivery catheter of claim 2, further comprising:
   a clock device having operational circuitry configured to record a dispensing time of the fluid into the cavity of the distal holding section.

4. The delivery catheter of claim 3, wherein the clock device is operationally coupled to the user interface and the operational circuitry of the clock device is further configured to:
   send the dispensing time to the display.

5. The delivery catheter of claim 4, wherein the pressure sensing flow-sensing device is operationally coupled to the clock device.

6. The delivery catheter of claim 5, wherein the operational circuitry of the flow-sensing device is further configured to:
   receive the dispensing time from the clock device.

7. The delivery catheter of claim 6, wherein the operational circuitry of the flow-sensing device is further configured to:
   send the first signal to the display indicating an acceptable deployment location; and
   send the second signal to the display indicating an unacceptable deployment location.

8. The delivery catheter of claim 7, wherein the first signal is sent in response to an inclusion of the pressure or flow-rate in a range of values, within the dispensing time and the second signal is sent in response to a non-inclusion of the pressure or flow-rate in the range of values, within the dispensing time.

9. A method of delivering an implantable leadless pacing device using a flow-sensing device having operational circuitry, the method comprising:
   dispensing a fluid into a cavity of a distal holding section of a delivery system through a catheter shaft secured to a proximal end of the distal holding section while a leadless pacing device is present in the cavity;
   observing the cavity of the distal holding section using the flow-sensing device in response to the dispensing of the fluid;
   determining a pressure or flow-rate of the fluid within the holding section based on the observation of the cavity, wherein the pressure or flow-rate indicates wall apposition between a distal end of the distal holding section and a heart chamber wall; and sending a signal indicative of the pressure or flow-rate to a display of a user interface based on the determinations;

wherein inclusion of the pressure or flow-rate in a range of values indicates the wall apposition is acceptable and non-inclusion of the pressure or flow-rate in the range of values indicates the wall apposition is unacceptable.

10. The method of claim 9, wherein the acceptable wall apposition indicates an acceptable deployment location for the implantable leadless pacing device and the unacceptable wall apposition indicates an unacceptable deployment location for the implantable leadless pacing device.

11. The method of claim 9, further comprising:
recording a dispensing time of the fluid into the cavity of the distal holding section using a clock device.

12. The method of claim 11, wherein the clock device is operationally coupled to the user interface and the method further comprises:
sending the dispensing time to the display using the clock device.

13. The method of claim 11, wherein the flow-sensing device is operationally coupled to the clock device and the method further comprises:
sending the dispensing time to the flow-sensing device, using the clock device;
sending a first signal to the display indicating an acceptable deployment location, using the flow-sensing device; and
sending a second signal to the display indicating an unacceptable deployment location, using the flow-sensing device.

14. The method of claim 13, wherein the first signal is sent in response to an inclusion of the pressure or flow-rate in the range of values, within the dispensing time and the second signal is sent in response to a non-inclusion of the pressure or flow-rate in the range of values, within the dispensing time.

15. A delivery device for delivering an implantable leadless pacing device, the delivery device comprising:
a catheter shaft extending from a proximal end to a distal end thereof, the catheter shaft including a distal holding section defining a cavity therein for receiving the implantable leadless pacing device;
a clock device having operational circuitry configured to record a dispensing time of a fluid into the cavity of the distal holding section and send the dispensing time to a display on a user interface;
a flow-sensing device having operational circuitry configured to:
determine a pressure or flow-rate of the fluid within the cavity of the distal holding section,
send the pressure or flow-rate to the display, and
determine a correlation between the pressure or flow-rate and the dispensing time, wherein the correlation indicates a degree of wall apposition between a distal end of the distal holding section and a heart chamber wall;
a handle assembly including at least a hub portion affixed adjacent to the proximal end of the catheter shaft; and
a deployment mechanism disposed within the handle assembly;
wherein the deployment mechanism is configured to deploy the implantable leadless pacing device;
wherein an acceptable degree of wall apposition indicates an acceptable deployment location for the implantable leadless pacing device and an unacceptable degree wall apposition indicates an unacceptable deployment location for the implantable leadless pacing device.

16. The delivery device of claim 15, wherein the operational circuitry of the flow-sensing device is further configured to:
send a first signal to the display indicating the acceptable deployment location; and
send a second signal to the display indicating the unacceptable deployment location.

17. The delivery device of claim 16, wherein the first signal is sent in response to an inclusion of the pressure or flow-rate in a range of values, within the dispensing time and the second signal is sent in response to a non-inclusion of the pressure or flow-rate in the range of values, within the dispensing time.

* * * * *